(12) United States Patent
Murphy et al.

(10) Patent No.: US 10,085,966 B2
(45) Date of Patent: Oct. 2, 2018

(54) COMPOSITIONS AND METHODS FOR SKIN CARE

(71) Applicant: Antipodean Pharmaceuticals, Inc., Auckland (NZ)

(72) Inventors: Michael Patrick Murphy, Cambridge (GB); Robin A. J. Smith, Dunedin (NZ); Kenneth Martin Taylor, Auckland (NZ)

(73) Assignee: Antipodean Pharmaceuticals, Inc., Auckland (NZ)

( * ) Notice: Subject to any disclaimer, the term of this patent is extended or adjusted under 35 U.S.C. 154(b) by 0 days.

(21) Appl. No.: 15/400,510

(22) Filed: Jan. 6, 2017

(65) Prior Publication Data

US 2017/0340603 A1 Nov. 30, 2017

Related U.S. Application Data

(63) Continuation of application No. 12/410,318, filed on Mar. 24, 2009, now abandoned.

(60) Provisional application No. 61/041,551, filed on Apr. 1, 2008.

(51) Int. Cl.
| | |
|---|---|
| *A61K 31/66* | (2006.01) |
| *A61K 8/02* | (2006.01) |
| *A61K 31/355* | (2006.01) |
| *A61K 31/203* | (2006.01) |
| *A61K 31/375* | (2006.01) |
| *A61K 31/385* | (2006.01) |
| *A61Q 19/08* | (2006.01) |

(Continued)

(52) U.S. Cl.
CPC .............. *A61K 31/355* (2013.01); *A61K 8/55* (2013.01); *A61K 31/203* (2013.01); *A61K 31/375* (2013.01); *A61K 31/385* (2013.01); *A61K 31/66* (2013.01); *A61K 45/06* (2013.01); *A61Q 19/08* (2013.01); *A61K 2800/522* (2013.01)

(58) Field of Classification Search
CPC ....... A61K 31/66; A61K 9/004; A61K 9/0014
USPC .......................................... 514/125; 424/401
See application file for complete search history.

(56) References Cited

U.S. PATENT DOCUMENTS

| | | | |
|---|---|---|---|
| 5,869,703 | A | 2/1999 | Kim et al. |
| 5,922,335 | A | 7/1999 | Ptchelintsev |
| 6,261,544 | B1 | 7/2001 | Coury et al. |

(Continued)

FOREIGN PATENT DOCUMENTS

| | | |
|---|---|---|
| CN | 1282334 A | 1/2001 |
| EP | 1 371 640 A1 | 12/2003 |

(Continued)

OTHER PUBLICATIONS

Bauerova et al. "Chemical enhancers for transdermal drug transport," European Journal of Drug Metabolism and Pharmacokinetics, 2001, vol. 26, No. 12, pp. 85-94.*

(Continued)

*Primary Examiner* — Shengjun Wang
(74) *Attorney, Agent, or Firm* — Seed IP Law Group LLP

(57) ABSTRACT

Compositions and methods are for disclosed for treating a skin condition that results from reactive oxygen species production in skin of a subject, including applying a topical formulation that contains a lipophilic cation-mitochondrially targeted antioxidant compound and that delivers a therapeutically effective amount of the antioxidant compound to skin fibroblasts and keratinocytes.

19 Claims, 4 Drawing Sheets

(51) Int. Cl.
*A61K 8/55* (2006.01)
*A61K 45/06* (2006.01)

(56) References Cited

U.S. PATENT DOCUMENTS

| | | | |
|---|---|---|---|
| 6,387,882 B1 | 5/2002 | Ogata et al. | |
| 6,756,045 B1 | 6/2004 | Neudecker et al. | |
| 6,951,887 B2 | 10/2005 | Bingham et al. | |
| 7,205,003 B2 | 4/2007 | Maibach et al. | |
| 2002/0044913 A1* | 4/2002 | Hamilton | A61K 8/355 424/59 |
| 2005/0227957 A1 | 10/2005 | Murphy et al. | |
| 2006/0229278 A1* | 10/2006 | Taylor | C07F 9/5442 514/58 |
| 2007/0238709 A1 | 10/2007 | Murphy et al. | |
| 2008/0161267 A1 | 7/2008 | Taylor et al. | |

FOREIGN PATENT DOCUMENTS

| | | |
|---|---|---|
| EP | 1 267 823 B1 | 6/2005 |
| EP | 2 145 623 A1 | 1/2010 |
| GB | 1 466 062 A | 3/1977 |
| GB | 1466062 * | 3/1977 |
| JP | 2-157287 A | 6/1990 |
| JP | 02-157287 A * | 6/1990 |
| JP | 2005-507406 A | 3/2005 |
| WO | 94/00098 A1 | 1/1994 |
| WO | 94/00109 A1 | 1/1994 |
| WO | 99/26954 A1 | 6/1999 |
| WO | 01/74328 A2 | 10/2001 |
| WO | 03/037291 A1 | 5/2003 |
| WO | 2005/019232 A1 | 3/2005 |
| WO | 2005/019233 A1 | 3/2005 |
| WO | 2005/032544 A1 | 4/2005 |
| WO | 2006/065920 A1 | 6/2006 |
| WO | WO 2006/065920 A1 * | 6/2006 |
| WO | 2007/046729 A1 | 4/2007 |
| WO | WO2007/046729 A1 * | 4/2007 |
| WO | 2008/094061 A1 | 8/2008 |

OTHER PUBLICATIONS

Bakry et al., "Medicinal applications of fullerenes," *International Journal of Nanomedicine* 2(4):639-649, 2007.
Bauerová et al., "Chemical enhancers for transdermal drug transport," *European Journal of Drug Metabolism and Pharmacokinetics* 26(1/2):85-94, 2001.
Berneburg et al., "Singlet Oxygen Mediates the UVA-Induced Generation of the Photoaging-associated Mitochondrial Common Deletion," *The Journal of Biological Chemistry* 274(22):15345-15349, 1999.
Buettner, "The Pecking Order of Free Radicals and Antioxidants: Lipid Peroxidation, α-Tocopherol, and Ascorbate," *Archives of Biochemistry and Biophysics* 300(2):535-543, 1993.
Campo et al., "Purified human chondroitin-4-sulfate reduced MMP/TIMP imbalance induced by iron plus ascorbate in human fibroblast cultures," *Cell Biology International* 30:21-30, 2006.
Farris, "Idebenone, green tea, and Coffeeberry® extract: new and innovative antioxidants," *Dermatologic Therapy* 20:322-329, 2007.
Fisher et al., "Retinoic Acid Inhibits Induction of c-Jun Protein by Ultraviolet Radiation that Occurs Subsequent to Activation of Mitogen-activated Protein Kinase Pathways in Human Skin In Vivo," *J. Clin. Invest.* 101(6):1432-1440, 1998.
Griffiths et al., "Mechanisms of action of retinoic acid in skin repair," *British Journal of Dermatology* 127(Supplement 41):21-24, 1992.
Jauslin et al., "Mitochondria-targeted antioxidants protect Friedreich Ataxia fibroblasts from endogenous oxidative stress more effectively than untargeted antioxidants," *The FASEB Journal* 17(13):1972-1974, 2003.
Kang et al., "Topical N-Acetyl Cysteine and Genistein Prevent Ultraviolet-Light-Induced Signaling That Leads to Photoaging in Human Skin in vivo," *The Journal of Investigative Dermatology* 120(5):835-841, 2003.
Kohen, "Skin antioxidants: their role in aging and in oxidative stress—New approaches for their evaluation," *Biomed & Pharmacother* 53:181-192, 1999.
Matsunaga et al., "Involvement of activation of NADPH oxidase and extracellular signal-regulated kinase (ERK) in renal cell injury induced by zinc," *The Journal of Toxicological Sciences* 30(2):135-144, 2005.
McDaniel et al., "Clinical efficacy assessment in photodamaged skin of 0.5% and 1.0% idebenone," *Journal of Cosmetic Dermatology* 4:167-173, 2005.
McDaniel et al., "Idebenone: a new antioxidant—Part I. Relative assessment of oxidative stress protection capacity compared to commonly known antioxidants," *Journal of Cosmetic Dermatology* 4:10-17, 2005.
Noda et al., "Antioxidant Activities of Novel Alpha-Lipoic Acid Derivatives: N-(6, 8-Dimercaptooctanoyl)-2-Aminoethanesulfonate- and N-(6, 8-dimercaptooctanoyl)-L-Aspartate-Zinc Complex," *Res. Comm. Mol. Path. Pharmacol.* 113-114:133-147, 2003.
Schroeder et al., "Cellular response to infrared radiation involves retrograde mitochondrial signaling," *Free Radical Biology & Medicine* 43:128-135, 2007.
Schroeder et al., "Partial Depletion of Mitochondrial DNA from Human Skin Fibroblasts Induces a Gene Expression Profile Reminiscent of Photoaged Skin," *Journal of Investigative Dermatology* 128:2297-2303, 2008.
Tournas et al., "Ubiquinone, Idebenone, and Kinetin Provide Ineffective Photoprotection to Skin when Compared to a Topical Antioxidant Combination of Vitamins C and E with Ferulic Acid," *Journal of Investigative Dermatology* 126:1185-1187, 2006.
Valko et al., "Free radicals and antioxidants in normal physiological functions and human disease," *The International Journal of Biochemistry & Cell Biology* 39:44-84, 2007.
Xu et al., "Epidermal Growth Factor Receptor Is a Critical Mediator of Ultraviolet B Irradiation-Induced Signal Transduction in Immortalized Human Keratinocyte HaCaT Cells," *The American Journal of Pathology* 169(3):823-830, 2006.
Xu et al., "Oxidative Inhibition of Receptor-type Protein-tyrosine Phosphatase κ by Ultraviolet Irradiation Activities Epidermal Growth Factor Receptor in Human Keratinocytes," *The Journal of Biological Chemistry* 281(37):27389-27397, 2006.

* cited by examiner

COMPOSITIONS AND METHODS FOR SKIN CARE

CROSS-REFERENCE TO RELATED APPLICATION

This application is a continuation of U.S. patent application Ser. No. 12/410,318, filed Mar. 24, 2009; which claims the benefit under 35 U.S.C. § 119(e) of U.S. Provisional Patent Application No. 61/041,551 filed Apr. 1, 2008; which applications are incorporated herein by reference in their entirety.

BACKGROUND

Technical Field

The present invention relates generally to biomedical compositions and methods for treating diseases, disorders and conditions affecting skin. In particular, the present invention provides compositions and methods for treating skin conditions that result from reactive oxygen species production in human skin, such as photoaging and other age-related skin damage, by highly effective delivery of antioxidants to skin fibroblasts and keratinocytes, including delivery to mitochondria in these cell types.

Description of the Related Art

In higher vertebrates including mammals and particularly in humans, skin is the largest body organ and serves as an important environmental interface, providing a protective envelope that is crucial for homeostasis. The outer layer of skin, the epidermis, is covered by the stratum corneum, a protective layer of dead epidermal skin cells (e.g., keratinocytes) and extracellular connective tissue proteins that is continually being sloughed off as it is replaced by new material pushed up from the underlying epidermal granular cell, spinous cell, and basal cell layers, where continuous cell division and protein synthesis produce new skin cells and skin proteins (e.g., keratin, collagen). Beneath the epidermis lies the dermis, in which dermal fibroblasts elaborate connective tissue proteins (e.g., collagen, elastin, etc.) that assemble into extracellular matrix and fibrous structures that give skin its flexibility, strength and elasticity. Nerves, blood vessels, smooth muscle cells, hair follicles and sebaceous glands are also present in the dermis.

Skin provides physicochemical protection against environmental insults through its barrier function, mechanical strength and imperviousness to water. Epidermal dendritic (Langerhans) cells, and migrating as well as resident white blood cells in the skin (e.g., lymphocytes, macrophages, mast cells) contribute to immunological protection while pigmented melanocytes in the basal layer absorb potentially harmful ultraviolet (UV) radiation.

Skin is also, however, a major target for toxic insult by a broad spectrum of physical (e.g., UV radiation) and chemical (e.g., xenobiotic) agents that are capable of altering its structure and function. Oxidative stress has been implicated as a major mediator of both natural skin aging and photoaging (accelerated skin aging due to UV exposure), which are typically accompanied by one or more undesirable effects such as wrinkling, dryness, itching, sagging, changes in texture, pigmentation or thickness, appearance of superficial blood vessels, appearance of growths including benign and precancerous lesions, and other sequelae. In natural aging including skin aging, oxidative stress derives from aerobic oxidative metabolism, which occurs in all human cells, and is required to maintain life. In skin photoaging, oxidative stress derives from photochemical conversion of electromagnetic energy into chemically reactive oxygen species (ROS) within skin cells exposed to solar UV irradiation. See, e.g., Mayachi, Skin Diseases Associated with Oxidative Injury, in Oxidative Stress in Dermatology, J. Fuchs (Ed.), Marcel Dekker, Inc., NY, 1993, pp. 323ff.

Oxidative stress sets in motion a complex array of cellular responses (e.g., Xu et al., 2006 $Am.\ J.\ Pathol.$ 169:823; Xu et al., 2006 $J.\ Biol.\ Chem.$ 281:27389). Among these responses is activation of signal transduction pathways that result in increased production of matrix metalloproteinases. Matrix metalloproteinases degrade the collagenous extracellular matrix that comprises skin connective tissue (dermis). Degradation of dermal extracellular matrix, which is composed primarily of type I collagen, impairs the structural integrity of the skin, and is largely responsible for the thin, wrinkled appearance of aged and photoaged skin. (Fisher et al., 2002 $Arch.\ Dermatol.$ 138:1462).

Additionally, many environmental pollutants are either themselves oxidants, or else catalyze the production of reactive oxygen species (ROS) directly or indirectly. ROS are believed to activate cytoproliferative and/or cell survival signaling mechanisms, including mechanisms that can alter (e.g., up- or down-regulate in a statistically significant manner) apoptotic and other regulated pathways that may be involved in the pathogenesis of a number of skin disorders, including photosensitivity diseases and some types of cutaneous malignancy.

The skin possesses an array of defense mechanisms that interact with toxicants to obviate their deleterious effects. These protective mechanisms include non-enzymatic and enzymatic molecules that function as potent antioxidants or oxidant-degrading systems. Unfortunately, these homeostatic defenses, although highly effective, have limited capacity and can be overwhelmed, thereby leading to increased ROS in the skin that can foster the development of dermatological diseases.

A number of approaches to preventing or treating these ROS-mediated disorders in skin are based on the direct topical administration of various antioxidants in an effort to block oxidative damage of protein, DNA and phospholipids in tissues and cells, to restore physiological homeostasis (e.g., Farris, 2007 $Dermatol.\ Ther.$ 20:322; Kang et al., 2003 $J.\ Invest.\ Dermatol.$ 120:835; Kohen, 1999 $Biomed.\ Pharmacother.$ 53:181). Such antioxidants include topical N-acetyl cysteine (e.g., Kang et al., 2003 $J.\ Invest.\ Dermatol.$ 120:835), and other antioxidants typically based on the predominant form of human ubiquinone, Coenzyme Q10 (CoQ10). CoQ10, however, is a physiologically untargeted compound that generally exhibits poor bioavailability, at least in part due to its high degree of hydrophobicity, making it difficult to achieve protective levels of CoQ10 antioxidant activity at sites of oxidative damage.

Another untargeted antioxidant is the artificial ubiquinone, idebenone, a Coenzyme Q10 analogue. Idebenone has been shown to have antioxidant effects based on its ability to protect against cell damage from oxidative stress in a variety of biochemical, cell biological and in vivo methods (e.g., U.S. Pat. No. 6,756,045), including its ability as a topical agent to suppress sunburn cell formation in living skin (McDaniel et al., 2005 $J.\ Cosmet.\ Dermatol.$ 4:10; see also review by Farris, 2007 $Dermatol.\ Ther.$ 20:322). Idebenone has also been reported to protect skin from damage in a controlled clinical trial as a topical cream (McDaniel et al., 2005 $J.\ Cosmet.\ Dermatol.$ 4:167), although its effectiveness as an antioxidant skin photoprotectant has been called into question (Tournas et al., 2006 $J.\ Invest.\ Dermatol.$ 126:1185). Idebenone is available topically as a cosmetic (Prevage®) and is marketed by Allergan and Elizabeth Arden. As an untargeted antioxidant, however, idebenone lacks the ability to deliver high local concentrations of antioxidant activity to tissue, cellular and subcellular sites where oxidative damage may be occurring. For example, when tested on skin fibroblasts higher concentrations of idebenone than of CoQ10 were required to obtain significant cytoprotective effects, and neither compound was capable of accumulation in mitochondria, which are major sites for ROS generation (Jauslin et al., 2003 *FASEB J.* 17:1972). A large number of topical dermatologic products purport to protect skin against photoaging using antioxidants but generally provide only low concentrations of antioxidant compounds and exhibit poor absorption into the skin (Kang et al., 2003 *J. Invest. Dermatol.* 120:835; Tournas et al., 2006 *J. Invest. Dermatol.* 126:1185). Additionally, beneficial delivery, by untargeted antioxidants such as CoQ10 or idebenone, of antioxidant activity to other skin cell types remains to be demonstrated.

Multiple complex cellular respiratory, oxidative and metabolic processes are regulated in and by mitochondria, the principle cellular energy source in higher organisms. These processes include electron transport chain (ETC) activity, which drives oxidative phosphorylation to produce metabolic energy in the form of adenosine triphosphate (ATP), and which also underlies a central mitochondrial role in intracellular calcium homeostasis.

Highly reactive free radicals that have the potential for damaging cells and tissues may result from altered or defective mitochondrial activity, including but not limited to failure at any step of the ETC. These free radicals may include reactive oxygen species (ROS) such as superoxide, peroxynitrite and hydroxyl radicals, and potentially other reactive species that may be toxic to cells. For example, UV-induced signal transduction and ROS generation have been shown to induce matrix metalloproteinase (MMP) expression in human skin as part of a molecular mechanism underlying photoaging (Kang et al., 2003 *J. Invest. Dermatol.* 120:835).

Clearly there is a need in the art for improved compositions and methods for treating skin conditions that result from ROS generation and oxidative damage, including effective delivery of antioxidants to skin sites of ROS production such as keratinocyte and fibroblast mitochondria. The presently disclosed invention embodiments address this need and offer other related advantages.

BRIEF SUMMARY

According to certain embodiments of the present invention, there is provided a method of treating a skin condition that results from reactive oxygen species production in skin of a subject, the method comprising applying to the skin a topical formulation that comprises (a) an antioxidant compound which comprises (i) a lipophilic cationic moiety linked by a linking moiety to an antioxidant moiety, and (ii) an anionic complement for said cationic moiety, and (b) a pharmaceutical excipient or carrier for topical use, wherein the formulation delivers a therapeutically effective amount of the antioxidant compound to skin fibroblasts and keratinocytes and the cationic moiety is capable of mitochondrially targeting the antioxidant moiety, and wherein the anionic complement is a pharmaceutically acceptable anion that is not a bromide ion or a nitrate anion and does not exhibit reactivity against the antioxidant moiety, the cationic moiety or the linking moiety, and thereby treating the skin condition that results from reactive oxygen species production in skin. In certain embodiments the antioxidant moiety comprises at least one antioxidant moiety that is selected from (i) a quinone or a quinol, (ii) vitamin E or a vitamin E derivative, (iii) ascorbic acid or an ascorbic acid derivative, (iv) alpha-lipoic acid or a derivative thereof, (v) a chain breaking antioxidant, (vi) a derivatized fullerene, (vii) a spin trap, (viii) an antioxidant moiety that is selected from the group consisting of butylated hydroxyanisole, butylated hydroxytoluene, 5,5-dimethylpyrroline-N-oxide, tent-butyl-nitrosobenzene, tert-nitrosobenzene and α-phenyl-tert-butylnitrone, and (ix) N-acetyl cysteine. In certain embodiments the topical formulation further comprises retinoic acid. In certain embodiments the antioxidant compound is capable of altering (i) a detectable indicator of reactive oxygen species in a human skin fibroblast, and (ii) a detectable indicator of reactive oxygen species in a human skin keratinocyte. In certain embodiments the lipophilic cationic moiety is a triphenylphosphonium cation. In certain embodiments the pharmaceutically acceptable anion is not a halogen ion. In certain embodiments the pharmaceutically acceptable anion is not nucleophilic. In certain embodiments the pharmaceutically acceptable anion is an alkyl sulfonate. In certain embodiments the pharmaceutically acceptable anion is selected from methanesulfonate, p-toluenesulfonate, ethanesulfonate, benzenesulfonate and 2-naphthalenesulfonate. In certain embodiments the pharmaceutically acceptable anion is methanesulfonate. In certain embodiments the antioxidant compound has the formula I:

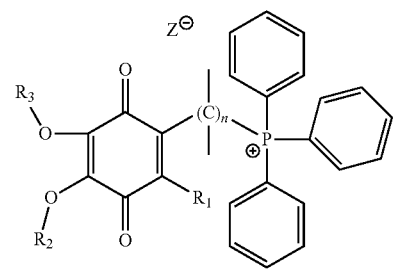

or its quinol form, wherein $R_1$, $R_2$, and $R_3$ are the same or different and are selected from $C_1$ to $C_5$ alkyl and H, and wherein n is an integer from 2 to 20, and wherein Z is the anionic complement. In certain further embodiments Z is selected from an alkyl sulfonate, an aryl sulfonate and nitrate. In certain embodiments C of $(C)_n$ is saturated.

In certain embodiments of the above described methods the antioxidant compound has the formula:

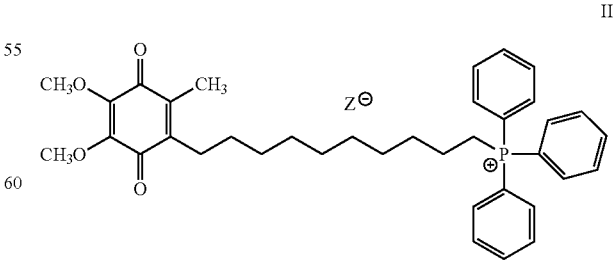

or its quinol form, wherein Z is the anionic complement.

In certain embodiments the antioxidant compound has the formula:

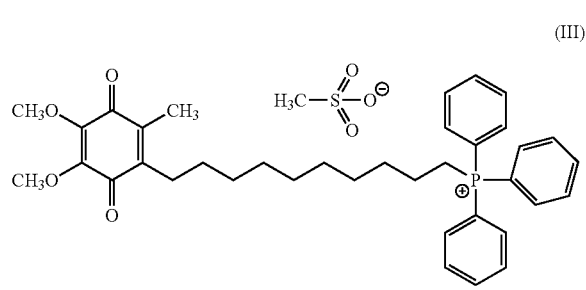

(III)

or its quinol form.

In certain embodiments the pharmaceutical excipient or carrier comprises cyclodextrin. In certain further embodiments the antioxidant compound and cyclodextrin are present at a compound-to-cyclodextrin molar ratio that is from about 10:1 to about 1:10. In certain other further embodiments the antioxidant compound and cyclodextrin are present at a compound-to-cyclodextrin molar ratio that is selected from the group consisting of (i) from about 5:1 to about 1:5, (ii) from about 4:1 to about 1:4, (iii) from about 2:1 to about 1:2, (iv) about 1:1 and (v) about 1:2. In certain embodiments the cyclodextrin is β-cyclodextrin. In certain embodiments the antioxidant compound and cyclodextrin are present at a compound-to-cyclodextrin molar ratio that is about 1:2.

In certain embodiments of the above described methods, the skin condition that results from reactive oxygen species production is characterized by alteration of at least one of (i) a detectable indicator of reactive oxygen species in a human skin fibroblast, and (ii) a detectable indicator of reactive oxygen species in a human skin keratinocyte. In certain other embodiments the skin condition that results from reactive oxygen species production is characterized by alteration of (i) a detectable indicator of reactive oxygen species in a human skin fibroblast, and (ii) a detectable indicator of reactive oxygen species in a human skin keratinocyte. In certain embodiments the skin condition that results from reactive oxygen species production is age-related skin damage. In certain further embodiments the age-related skin damage comprises skin photoaging. In certain further embodiments skin photoaging comprises one or more of wrinkling, scar tissue deposition, altered skin elasticity, altered skin color, altered skin texture, altered skin thickness, angioma, telangiectasia, sunburn, dryness, itchiness, neoplasia and precancerous growth. In certain other related embodiments the skin condition that results from reactive oxygen species production comprises a skin infection. In certain further embodiments the skin infection comprises at least one of a bacterial infection, a viral infection, a parasitic infection and a fungal infection.

In certain other embodiments the skin condition that results from reactive oxygen species production comprises one or more of acne, amyloidosis, a benign skin tumor, a blister or ulcer, bullous disease, skin cancer, dermatitis, eczema, inflammation, ichthyosis, an insect bite or insect sting, keratosis pilaris, pruritis, psoriasis, a scaling disease, a rash, vitiligo and a sweat gland disorder. In certain embodiments the antioxidant compound is capable of altering (i) at least one detectable indicator of reactive oxygen species in a human skin fibroblast that is selected from the group consisting of reactive oxygen species generation, matrix metalloproteinase expression and an extracellular signal-related kinase (ERK) phosphorylation state, and (ii) at least one detectable indicator of reactive oxygen species in a human skin keratinocyte that is selected from the group consisting of reactive oxygen species generation, matrix metalloproteinase expression and an extracellular signal-related kinase (ERK) phosphorylation state. In certain other embodiments the skin condition that results from reactive oxygen species production comprises one or more condition selected from the group consisting of erythema, skin redness and inflammation caused by laser surgery, radiation therapy, sun burn, rosaceae, a burn or sepsis.

According to certain other embodiments there is provided a method of promoting topical wound healing in skin of a subject, the method comprising applying to the skin a topical formulation that comprises (a) an antioxidant compound which comprises (i) a lipophilic cationic moiety linked by a linking moiety to an antioxidant moiety, and (ii) an anionic complement for said cationic moiety, and (b) a pharmaceutical excipient or carrier for topical use, wherein the formulation delivers a therapeutically effective amount of the antioxidant compound to skin fibroblasts and keratinocytes and the cationic moiety is capable of mitochondrially targeting the antioxidant moiety, and wherein the anionic complement is a pharmaceutically acceptable anion that is not a bromide ion or a nitrate anion and does not exhibit reactivity against the antioxidant moiety, the cationic moiety or the linking moiety, and thereby treating the skin condition that results from reactive oxygen species production in skin. In certain further embodiments the antioxidant moiety comprises at least one antioxidant moiety that is selected from the group consisting of (i) a quinone or a quinol, (ii) vitamin E or a vitamin E derivative, (iii) ascorbic acid or an ascorbic acid derivative, (iv) alpha-lipoic acid or a derivative thereof, (v) a chain breaking antioxidant, (vi) a derivatized fullerene, (vii) a spin trap, (viii) an antioxidant moiety that is selected from the group consisting of butylated hydroxyanisole, butylated hydroxytoluene, 5,5-dimethylpyrroline-N-oxide, tert-butylnitrosobenzene, tert-nitrosobenzene and α-phenyl-tert-butylnitrone, and (ix) N-acetyl cysteine. In certain embodiments the topical formulation further comprises retinoic acid. In certain embodiments the antioxidant compound is capable of altering (i) a detectable indicator of reactive oxygen species in a human skin fibroblast, and (ii) a detectable indicator of reactive oxygen species in a human skin keratinocyte. In certain embodiments the lipophilic cationic moiety is a triphenylphosphonium cation. In certain embodiments the pharmaceutically acceptable anion is not a halogen ion. In certain embodiments the pharmaceutically acceptable anion is not nucleophilic. In certain embodiments the pharmaceutically acceptable anion is an alkyl sulfonate. In certain embodiments the pharmaceutically acceptable anion is selected from methanesulfonate, p-toluenesulfonate, ethanesulfonate, benzenesulfonate and 2-naphthalenesulfonate. In certain embodiments the pharmaceutically acceptable anion is methanesulfonate.

These and other aspects of the invention will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet, are incorporated herein by reference in their entirety, as if each was incorporated individually. Aspects of the invention can be modified, if necessary, to employ concepts of the various patents, applications and publications to provide yet further embodiments of the invention.

DETAILED DESCRIPTION

Figure 1:
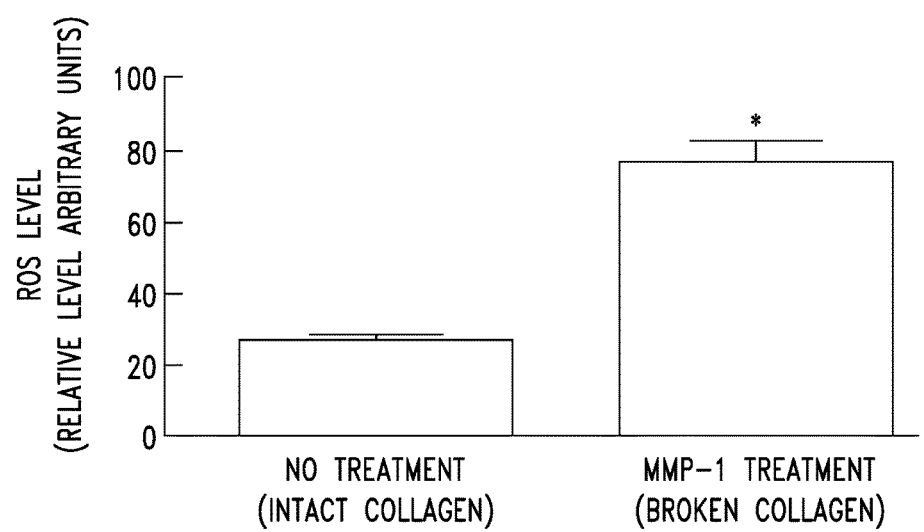
FIG. 1 shows induction of ROS production in human skin fibroblasts cultured in three-dimensional collagen lattices, following treatment with collagenase (MMP1).

Certain embodiments of the invention disclosed herein are based on the surprising discovery that an antioxidant compound as described herein, which comprises a cationic moiety that is capable of mitochondrially targeting a linked antioxidant moiety, can be formulated into a topical formulation that delivers a therapeutically effective amount of the antioxidant compound to skin fibroblasts and keratinocytes.

In particular, it has been discovered that the antioxidant compounds of the topical formulations and treatment methods described herein unexpectedly biodistribute to, and are effective in, epidermal keratinocytes and dermal fibroblasts following topical administration to human skin, and do so in a manner that provides antioxidant activity to such cells and surrounding tissues at a level sufficient to confer therapeutic benefit. The applicants' discovery thus offers unprecedented and unforeseen advantages over previous efforts to deliver topically any antioxidant compound for treating a skin condition that results from reactive oxygen species production in skin, and may be regarded as especially noteworthy where no previously known topically administered antioxidant has been effectively delivered to, and has shown beneficial antioxidant activity in, both cell types, skin fibroblasts and keratinocytes. In addition, topical formulations containing the herein described antioxidant compounds provide effective pharmaceutical and cosmeceutical benefit using lower concentrations of the antioxidant compounds than are needed with previously described topical antioxidants.

Accordingly, certain preferred embodiments contemplate topical formulations that contain the herein described mitochondrially targeted antioxidant compounds for beneficial (e.g., therapeutically or cosmetically beneficial) use at concentrations that are lower (e.g., in a statistically significant manner) than the concentration required for any previously described topical antioxidant such as previously described topical antioxidants that lack the presently disclosed cationic moiety that is capable of mitochondrially targeting the antioxidant moiety. Such lower concentrations may be lower by at least 1%, 2%, 5%, 10%, 20%, 25%, 30%, 35%, 40%, 50%, 60%, 70%, 80%, 90%, 95% or more than the concentrations needed for a previously described topical antioxidant, such as previously described topical antioxidants that lack the presently disclosed cationic moiety that is capable of mitochondrially targeting the antioxidant moiety, to achieve a comparable therapeutic and/or cosmetic effect; certain related embodiments contemplate achieving such benefits at concentrations of the present mitochondrially targeted antioxidant compounds that may be less than one fiftieth, one one-hundreth, one five-hundreth, one one-thousandth, one five-thousandth, one ten-thousandth, or one twenty-thousandth the concentration needed for any previously described topical antioxidant that lacks the presently disclosed cationic moiety that is capable of mitochondrially targeting the antioxidant moiety, or lower, in view of the herein described accumulation in cellular mitochondria of the present mitochondrially targeted antioxidant compounds.

The embodiments disclosed herein thus include compositions and methods for treating a skin condition that results from reactive oxygen species production in skin of a subject, and particularly in skin fibroblasts and keratinocytes.

In certain preferred embodiments that relate to treating a skin condition that results from ROS production in skin of a subject, treating includes contacting the skin of the subject, for instance by directly applying to the skin a topical formulation as herein described, in a manner that affects the subject, and/or skin tissue in the subject and/or one or a plurality of cells, to obtain a desired pharmacologic effect and/or a physiologic effect and/or cosmetic effect. The effect may be prophylactic in terms of completely or partially preventing a disease or disorder such as a condition that results from ROS production in skin, or a sign or symptom thereof, and/or the effect may be therapeutic in terms of relieving symptoms or signs or providing a partial or complete cure for such a disorder or disease and/or substantially impairing an adverse effect attributable to the disorder or disease.

According to certain embodiments a method of treating therefore may include any treatment of, or prevention of, or inhibition of a disorder or disease in a subject, and in particularly preferred embodiments, a skin condition that results from ROS production in skin. The subject may be an invertebrate, a vertebrate, such as a mammal, including humans and non-human primates, and in particularly preferred embodiments is a human.

Related embodiments contemplate, by way of example: (i) preventing the disease or disorder (e.g., skin condition that results from ROS) from occurring in a subject that may be predisposed to the disease or disorder, but has not yet been diagnosed as having it; (ii) inhibiting the disease or disorder, i.e., arresting its progression; or (iii) relieving or ameliorating the disease or disorder, i.e., causing regression. Thus, treating as used herein includes, for example, repair and regeneration of damaged or injured tissue or cells such as at a site of age-related skin damage (e.g., photodamage) or prophylactic treatments to prevent such damage, for instance, prior to exposure of the subject to a source of oxidative stress that may promote ROS production in skin, such as UV radiation, chemical agents (including other topical agents such as medical, pharmaceutical or cosmetic compounds), or prior to chemotherapy.

As also noted above, the presently disclosed embodiments derive in part from the unexpected and surprising observation that a topical formulation comprising the antioxidant compound described herein delivers a therapeutically effective amount of the antioxidant to skin fibroblasts and keratinocytes. Hence, the antioxidant compound, which comprises a cationic moiety that is capable of mitochondrially targeting a linked antioxidant moiety, can permeate skin and be delivered to, and surprisingly exhibits antioxidant effects in, both cell types.

Neither from previous efforts to apply topical formulations of other antioxidant compounds, nor from previous characterization of the antioxidant compounds described herein, could it be predicted that the present formulations would have antioxidant effects on skin fibroblasts and keratinocytes, for use in treating a skin condition that results from ROS production in skin. Without wishing to be bound by theory, the retention by such compounds of effective antioxidant activity, following topical administration, permeation of the stratum corneum and absorption in the epidermis (including epidermal keratinocytes), and further following penetration to the dermal layer (including update by dermal fibroblasts), are regarded as unexpected. Further according to non-limiting theory, it is believed that the presently described therapeutic effect derives at least in part from mitochondrial targeting of the antioxidant moiety to mitochondria of skin fibroblasts and keratinocytes, but the therapeutic effects may also derive in part from extramitochondrial effects of the antioxidant compounds described herein (e.g., on cellular signal transduction pathway components) and/or from extracellular effects (e.g., on ROS effects in the extracellular matrix).

According to preferred embodiments there are provided compositions and methods directed to the use of a topical formulation that comprises (a) an antioxidant compound which comprises (i) a lipophilic cationic moiety linked by a linking moiety to an antioxidant moiety, and (ii) an anionic complement for the cationic moiety; and (b) a pharmaceutical carrier or excipient for topical use, wherein the topical formulation delivers a therapeutically effective amount of the antioxidant compound to skin fibroblasts and keratinocytes and the cationic moiety is capable of mitochondrially targeting the antioxidant moiety, and wherein the anionic complement is a pharmaceutically acceptable anion that is not a bromide ion or a nitrate anion and does not exhibit reactivity against the antioxidant moiety, the cationic moiety or the linking moiety, and thereby treating the skin condition that results from reactive oxygen species production in skin.

Preferred antioxidant compounds for use according to the embodiments described herein include those described herein and others that are known in the art and that are disclosed, for example, in WO 2005/019232, WO 2005/019233, U.S. Application Publication No. 2006/0229278 (U.S. application Ser. No. 11/355,518), U.S. Application Publication No. 2007/0238709 (U.S. application Ser. No. 10/568,654), and U.S. application Ser. No. 10/568,655, all of which are incorporated by reference, as noted above. Therein can be found additional details regarding the selection of a lipophilic cationic moiety, which in preferred embodiments may be triphenylphosphonium cation, and of an anionic complement for such a cationic moiety that is not nucleophilic and is not a halogen ion, and that may be an anion including a pharmaceutically acceptable anion such as an alkyl sulfonate (e.g., methanesulfonate, ethanesulfonate) or p-toluenesulfonate, benzenesulfonate, 2-napthaleneslfonate or the like, and of a linking moiety (e.g., a substituted or unsubstituted carbon chain of 2-20 carbon atoms, preferably 3-15 carbon atoms, more preferably 4, 5, 6, 7, 8, 9, 10, 11, 12, 13 or 14 atoms, including substituted linkers described herein and in the cited publications) for linking the cationic moiety to an antioxidant moiety.

The antioxidant moiety may be, in preferred embodiments, a quinone or quinol such as the quinone found in mitoquinone or ubiquinone (or its quinol form), and which in other preferred embodiments may be vitamin E or a vitamin E derivative (e.g., α-tocopherol, α-tocopherol succinate, α-tocopheral acetate, tocotrienol, α-tocopheryloxyacetic acid, α-tocopherol ether acetic acid analog [2,5,7,8-tetramethyl-2R-(4R,8R,12-trimethyltridecyl)chroman-6-yloxyacetic acid (α-TEA)], or derivatives disclosed in WO 2005/032544 and in U.S. Pat. Nos. 5,869,703 and 6,387,882), ascorbic acid or an ascorbic acid derivative (e.g., ascorbate salts, dehydroascorbic acid, ascorbylpalmitate, etc.), α-lipoic acid or a derivative thereof (e.g., sodium N-(6, '8-dimercaptooctanoyl)-2-amino ethanesulfonate- and sodium N-(6, 8-dimercaptooctanoyl)-L-aspartate (Noda et al., 2003 Res. Comm. Mol. Path. Pharmacol. 113:133; or compounds disclosed in U.S. Pat. No. 6,951,887 and in EP 1,371,640), another chain breaking antioxidant (e.g., Buettner 1993 Arch. Biochem. Biophys. 300:535), a derivatized fullerene (e.g., Bakry et al., 2007 Int. J. Nanomed. 2:639), a spin trap (e.g., as described in Halliwell and Gutteridge, Free Radicals In Biology and Medicine ($3^{rd}$. ed.) 1999, Oxford Univ. Press, or other spin traps known to the art) and/or another antioxidant moiety, for instance, butylated hydroxyanisole, butylated hydroxytoluene, 5,5-dimethylpyrroline-N-oxide, tert-butylnitrosobenzene, tert-nitrosobenzene, α-phenyl-tert-butylnitrone, or N-acetyl cysteine.

Thus in certain preferred embodiments, the artificial ubiquinone, MitoQ® ([10-(4,5-dimethoxy-2-methyl-3,6-dioxo-1,4-cyclohexadien-1-yl)decyl] triphenylphosphonium methanesulfonate; WO05/019232), is targeted to mitochondria by covalent attachment of the ubiquinone antioxidant moiety to a lipophilic triphenylphosphonium cation. Because of the large mitochondrial inner membrane electrochemical potential that is generated by chemiosmotic coupling of the electron transport chain (ETC) to mitochondrial oxidative phosphorylation, the MitoQ® triphenylphosphonium cations accumulate within cellular mitochondria at levels up to 1,000-fold greater than those achieved by non-targeted antioxidants such as Coenzyme Q or its non-targeted analogues (e.g., idebenone), enabling the antioxidant moiety to block lipid peroxidation and protect mitochondria from oxidative damage.

Pharmaceutical excipients or carriers for topical use are described herein and known in the art and can also be found in WO 2005/019232, WO 2005/019233, U.S. Application Publication No. 2006/0229278 (U.S. application Ser. No. 11/355,518), U.S. Application Publication No. 2007/0238709 (U.S. application Ser. No. 10/568,654), and U.S. application Ser. No. 10/568,655, and may in certain preferred embodiments include cyclodextrin (e.g., β-cyclodextrin). In certain related embodiments cyclodextrin may be present in a topical formulation that comprises the herein described antioxidant compound at a compound-to-cyclodextrin molar ratio that is from about 10:1 to about 1:10, and in certain other related embodiments such a compound-to-cyclodextrin molar ratio may be from about 5:1 to about 1:5, from about 4:1 to about 1:4, from about 2:1 to about 1:2, about 1:1 or about 1:2, where in the context of quantitative parameters "about" may be understood to reflect a quantitative variation that may be more or less than the recited value by 0.5 logarithmic units (e.g., "logs" or orders of magnitude), more preferably no more than 0.4 log units, more preferably no more than 0.3 log units, still more preferably no more than 0.2 log units, and most preferably no more than 0.1-0.15 log units.

Skin Conditions

The method of delivery of the topical formulation containing the antioxidant compound may vary, but typically involves application of a formulation of the invention to an area of skin prone to or affected by a skin condition that results from ROS production, such as age-related skin damage, e.g., photoaging or any other skin condition or disorder associated with, caused by, or affected by, intrinsic aging and/or extrinsic aging. The aging-related skin condition may, for example, involve wrinkles, age spots, sun damage (particularly UV radiation-induced oxidative stress), blemishes, hyperpigmented skin, age spots, increased skin thickness, loss of skin elasticity and collagen content and/or dry skin.

Embodiments of the present invention thus relate to pharmaceutical or beneficial cosmetic ("cosmeceutical") preparations which may be used in preventing, managing, or treating various skin conditions and in particular, skin conditions that result from ROS production in skin of a subject, which skin conditions may relate to problems created by diseases, infections, aging, exposure to the elements, or otherwise. One skilled in the art will appreciate that the following examples are merely representative of skin conditions that include skin conditions that result from ROS production in the skin of a subject, and that skin conditions other than those listed herein may be treated according to embodiments of the present invention. For example, embodiments of the present invention may be used to prevent, manage, or treat any of the following:

In preferred embodiments the compositions and methods disclosed herein will find use in treating or preventing age-related effects on the skin, which are often attributed to damage caused by oxygen free radicals. Oxygen free radicals can damage cells and are believed to accelerate cancers and age-related diseases. Age related skin damage can also be caused by years of sun damage, poor nutrition, high stress levels, exposure to environmental pollution, and certain lifestyle choices, such as cigarette smoking, alcohol or drug abuse. Representative examples of aging effects on the skin include, but are not limited to, dryness, itchiness, development of fine lines and wrinkles, thinning or thickening of the skin, loss of elasticity, increased sagging, loss of firmness, loss of color evenness (tone), changes in color or texture (including coarse or rough skin surface texture), areas of hyperpigmentation (often called age or liver spots), mottled pigmentation such as actinic purpura (purplish spots on the skin created by small hemorrhages), visible blood vessels including cherry angiomas (red dome-like formations on the skin) and telangiectasias (broken capillaries on the face), increased number of benign growths (e.g., seborrheic keratoses) and precancerous growths (e.g., actinic keratoses), loss of sweat and oil glands, hair loss, unwanted hair, and photoaging (such as where the sun ultraviolet light damages certain fibers in the skin called elastin, causing the skin to sag, stretch, and lose its ability to snap back after stretching).

Acne, including all types of acne involving the skin and its oil glands and hair follicles in all stages, may be another category of skin condition that can beneficially be treated by methods described herein, including, for example, acne vulgaris, acne rosacea (red rash predominantly on the face), acne keloides nuchae (shaving rash), acne conglobata, acne cosmetica (caused by cosmetics), acne fulmicans, acne medicamentosa (caused by starting or stopping a medicine), baby acne, chloracne (caused by exposure to chlorinated hydrocarbons), perorial dermatitis, or acne observed in endocrinologic conditions characterized by excess androgen secretion, and the like, in the active inflammatory (pustule-, papule-, comedone-forming) and noninflammatory (blackhead- and cyst-forming) phases, and post-inflammatory (healing, scarring, and scarred) phase.

The presently disclosed compositions (including topical formulations) and methods may also be used to treat amyloidosis, which is the accumulation of various insoluble proteins (amyloid) in various organs. Amyloidosis confined to the skin is called primary localised cutaneous amyloidosis, and includes, for example, lichen amyloidosis, and macular amyloidosis and nodular primary localised cutaneous amyloidosis.

The presently disclosed compositions (including topical formulations) and methods may also be used to treat bacterial skin infections, including, for example, boils, cellulitis, cutaneous abcess, erysipelas, erythasma, folliculitis, furuncles, carbuncles, hidradentis suppurativa, impetigo and echthyma, lymphadenitis, lymphangitis, necrotizing subcutaneous infection, invasive group A streptococcal disease, staphyloccocal scalded skin syndrome, syphilis, and paronychia.

The presently disclosed compositions (including topical formulations) and methods may also be used to treat benign (non-cancerous) skin tumors, including, for example, derbatofibroma, epidermal cysts, growth and malformation of the vessels, keloids, keratoacanthomas, lipomas, moles, seborrheic keratoses, skin tags, and vascular lesions.

The presently disclosed compositions (including topical formulations) and methods may also be used to treat blisters (see also, bullous diseases, infra), sores or ulcers, which may be caused a variety of conditions, diseases, or by exposure to physical elements, including, for example, burns, sun exposure, wounds, frostbite, loss of mobility (e.g., bed sores or pressure ulcers), canker sores, cold sores, impetigo, insect bites or stings, incontentia pigmenti, leukemia, skin cancer, diabetes, AIDS, circulatory disorders, connective tissue disorders, chronic granulomatous disease, granuloma inguinale, glanders, hyper-IgE syndrome, hypertension, mycosis fungoides, necrotizing fasciitis, rheumatoid arthritis, sickle cell anemia, sporotrichosis, *vibrio vulnificus*, wounds, Wegener's granulomatosis, venous stasis, and other conditions, diseases, or infections having similar etiologies. These may include bullous diseases, which are diseases generally characterized by blistering of the skin, and include, for example, bullous pemphigoid, dermatitis herpetiformis, epidermolysis bullosa acquisita, linear Immunoglobulin A disease, pemphigus foliaceous, pemphigus vulgaris, and cicatricial pemphigoid.

The presently disclosed compositions (including topical formulations) and methods may also be used to treat cancers of the skin and damage to the skin resulting from any type of cancer treatment (e.g., chemotherapy, radiotherapy, surgery, immunotherapy including bone marrow or hematopoietic grafting, GVHD, etc.). Examples of cancers of the skin include, for example, basal cell carcinoma, squameous cell carcinoma, malignant melanoma, Bowen's disease, Kaposi's sarcoma, dermatofibrosarcoma, Merkel cell carcinoma, and Paget's disease of the nipple.

The presently disclosed compositions (including topical formulations) and methods may also be used to treat dermatitis, which is often characterized as a superficial inflammation or rash of the skin characterized by redness, edema, oozing, crusting, scaling, and sometimes vesicles. Pruritis (itching) is common in dermatitis. Eczema is a term often used interchangeably with dermatitis. Examples of dermatitis or eczema include, for example atopic dermatitis (also called infantile or flexural eczema), contact dermatitis (including allergic and irritant), xerotic eczema (also referred to as asteatotic eczema, craquele or craquelatum, winter itch, or pruritis hiemalis), exfoliative dermatitis, hand and foot dermatitis, neurodermatitis (e.g., lichen simplex chronicus), seborrheic dermatitis (cradle cap in infants, dandruff), discoid eczema (also referred to as nummular eczema, exudative eczema, microbial eczema), dyshydrosis, venous eczema (gravitationa eczema, stasis dermatitis, varicose eczema stasis dermatitis, dermatitis herpetiformis (Duhring's Disease), autoeczematization (also referred to as id reaction, autosensitization), cercarial dermatitis (e.g., swimmer's itch or duck itch), urushiol-induced contact dermatitis, which is also called *toxicodendron* dermatitis and *rhus* dermatitis (e.g., poison oak, poison ivy, sumac), solar dermatitis, and housewife eczema.

The presently disclosed compositions (including topical formulations) and methods may also be used to treat fungal skin infections, which damage the skin in part because they live off keratin, a primary protein component of skin, hair, and nails. Examples of fungal skin infections include, but are not limited to, candidiasis (thrush), dermatophytoses, intertrigo, *tinea versicolor, tinea* pedis (athlete's foot), *tinea* cruris (jock itch), *tinea* corporis (ringworm on the body), *tinea* capitis (ringworm on the scalp), *tinea* faciei (face fungus), onchomycosis and paronychia (nail infections).

The presently disclosed compositions (including topical formulations) and methods may also be used to treat hair disorders, which include, for example, alopecia (both scarring and nonscarring), hirsutism, pseudofolliculitis barbae (ingrown hairs), and hair shaft disorders.

The presently disclosed compositions (including topical formulations) and methods may also be used to treat hypersensitivity, inflammatory, autoimmune disorders, and the like, which may include, for example, allergic reactions, acute febrile neutrophilic dermatosis, drug eruptions and reactions, dermatomyositis, erythema (e.g., erythema multiforme and erythema nodosum), granuloma annulare, hives, panniculits, pemphigus, pyoderman gangrenosum, Stevens-Johnson Syndrome, Toxic Epidermal Necrolysis, erythrodermia, discoid lupus erythematosus, systemic lupus erythematosus, sclerodoma, thrombocytopenic purpura, reaction to vaccination, and other diseases or conditions as mentioned herein or otherwise known to one skilled in the art, and thus the presently disclosed compositions (including topical formulations) and methods may also be used to treat erythema, skin redness, inflammation caused by laser surgery, radiation therapy, sun burn, or as occurs in skin conditions such as rosaceae, burns and/or sepsis.

The presently disclosed compositions (including topical formulations) and methods may also be used to treat ichthyosis, which is a family of dermatological conditions often characterized by scaly skin which can vaguely resemble the scales of a fish. These conditions are caused mainly by genetic abnormalities, and include, for example, ichthyosis bullosa of Siemens, ichthyosis vulgaris, ichthyosis lamellaris, X-linked ichthyosis, epidermolytic hyperkeratosis, ichthyosis acquisita, Harlequin type ichthyosis, Netherton's syndrome, Sjogren-Larsson Syndrome, ichthyosis erythrokeratoderma variabolis.

The presently disclosed compositions (including topical formulations) and methods may also be used to treat insect bites or stings or bites or stings of other arthropods, which may include, for example, bites and stings caused by fire ants, wasps, yellow jackets, hornets, bees, fleas, ticks, mites, bedbugs, spiders, mosquitos, etc.

The presently disclosed compositions (including topical formulations) and methods may also be used to treat keratosis pilaris, which is a very common genetic follicular condition that is manifested by the appearance of rough bumps on the skin, and may include, for example, keratosis pilaris *rubra* (red, inflamed bumps), alba (rough, bumpy skin with no irritation), *rubra* faceii (reddish rash on the cheeks) and related disorders.

The presently disclosed compositions (including topical formulations) and methods may also be used to treat parasitic skin infections and their potentially damaging effects on skin, which may include, for example, creeping eruption, cutaneous larva migrans, delusional parasitosis, lice infestation, scabies, sarcoidosis, trypanosomiasis, leishmaniasis, and African sleeping sickness.

The presently disclosed compositions (including topical formulations) and methods may also be used to treat photodamage from ionizing radiation, which may cause edema, vasodilation, lymphocytic and neutrophilic infiltration in the dermis, dyskeratotic keratinocytes, spongiosis of the epidermis, in addition to other conditions (e.g., age related) as mentioned herein or otherwise known to one skilled in the art.

The presently disclosed compositions (including topical formulations) and methods may also be used to treat pruritus, which refers generally to itching of the skin, and may result from many of the skin disorders, conditions, and infections as mentioned herein or otherwise known to one skilled in the art, and may also be used to treat prurigo, which refers to itchy disruptions of the skin, including, for example, prurigo nodularis, actinic prurigo, and Besnier's prurigo (also called contact dermatitis).

The presently disclosed compositions (including topical formulations) and methods may also be used to treat pustulosis, which is a skin condition often characterized by large fluid-filled blister-like areas called pustules, and includes, for example, pustulosis palmaris et plantaris, palmoplantor pustulosis, acropustulosis, exanthematous pustulosis, subcorneou pustulosis, neutrophilic pustulosis, sinovitis acne pustulosis hyperostosis osteomyelitis syndrome (SAPHO).

The presently disclosed compositions (including topical formulations) and methods may also be used to treat scaling diseases, which are commonly characterized by sharply marginated, scaling papules or plaques without wetness, crusts, fissures, and excoriations, and may include, for example, lichen planus, lichen sclerosus, parapsoriasis, pityriasis lichenoides (including chronica and et varioliformis *acuta*), pityriasis rosea, pityriasis rubra pilaris, psoriasis. Psoriasis is a common, noncontagious, chronic, inflammatory disease with unknown cause, and includes, for example, plaque psoriasis, Guttafe psoriasis, inverse psoriasis, erthrodermic psoriasis, psoriatic arthritis, scalp psoriasis, and nail psoriasis.

The presently disclosed compositions (including topical formulations) and methods may also be used to treat rashes, which are generally characterized by a change in the skin which affects its appearance or texture, and may cause the skin to change color, itch, become warm, bumpy, dry, cracked or blistered, swell and may be painful. The causes of a rash may vary widely, and include, for example, anxiety or stress, exposure to sun or heat, irritation (e.g., by physical abrasion or contact with chemical irritants such as some metals, cleaning solutions, detergents, cosmetics, perfumes, industrial chemicals, and latex rubber), lead poisoning, pregnancy, diapers, and any other skin conditions as mentioned herein or otherwise known to one skilled in the arts. Representative examples of itching and noninfections rashes may include, but are not limited to, dermatitis, drug rashes, erythema multiforme, erythema nodosum, granuloma annulare, itching, keratosis pilaris, lichen planus, pityriasis rosea, psoriasis, rosacea, and Toxic Epidermal Necrolysis.

The presently disclosed compositions (including topical formulations) and methods may also be used to treat vitiligo or leukoderma, which is often characterized as a chronic skin condition that causes loss of pigment, resulting in irregular pale patches of skin, and may include, for example, vitiligo vulgaris (i.e., common vitiligo), linear vitiligo, segmental vitiligo, trichrome vitilito, and inflammatory vitiligo. Sweating and gland disorders, which may include, for example, bromhidrosis, hyperhidrosis, miliaria, and prickly heat, may also be treated according to the presently disclosed methods.

The presently disclosed compositions (including topical formulations) and methods may also be used to treat viral skin diseases, which may include, for example, molluscum contagiosum caused by poxviruses, herpes simplex, fifth disease, roseola, common warts caused by human papillomaviruses (HPV), genital/anal warts (condylomata *acuminatum*), flat warts, palmar and plantar warts, mosiac warts, periungual warts, zoonotic diseases, chickenpox, smallpox, cold sores, measles, melioidosis, and shingles.

One skilled in the art will appreciate that these and related embodiments of the present invention may be used to prevent or treat skin conditions, disorders, complications, diseases, infections, or otherwise, other than those listed herein.

Topical Formulations

As noted above, the invention embodiments described herein relate to topical formulations of the described antioxidant compositions, which formulations comprise the antioxidant compounds in a pharmaceutically acceptable carrier, excipient or diluent and in a therapeutic amount, as disclosed herein, when administered topically to an animal, preferably a mammal, and most preferably a human.

Topical administration of the antioxidant compounds described herein, or their pharmaceutically acceptable salts, in pure form or in an appropriate pharmaceutical composition, can be carried out via any of the accepted modes of topical administration of agents for serving similar utilities. Topical application or administration of a composition means, in preferred embodiments, directly contacting the composition (e.g., a topical formulation) with skin of the subject undergoing treatment, which may be at one or more localized or widely distributed skin sites and which may generally refer to contacting the topical formulation with intact stratum corneum or epidermis but need not be so limited; for instance, certain embodiments contemplate as a topical application the administration of a topical formulation described herein to injured, abraded or damaged skin, or skin of a subject undergoing surgery, such that contact of the topical formulation may take place not only with stratum corneum or epidermis but also with skin granular cell, spinous cell, and/or basal cell layers, and/or with dermal or underlying tissues, for example, as may accompany certain types of wound repair or wound healing or other skin tissue remodeling.

The topical formulations (e.g., cosmeceutical and pharmaceutical compositions) of the invention may be prepared by combining the described antioxidant compound with an appropriate pharmaceutically acceptable carrier, diluent or excipient for use in a topical formulation preparation, and may be formulated into preparations in solid, semi-solid, gel, cream, colloid, suspension or liquid or other topically applied forms, such as powders, granules, ointments, solutions, washes, gels, pastes, plasters, paints, bioadhesives, microsphere suspensions, and aerosol sprays. Pharmaceutical compositions of the invention are formulated so as to allow the active ingredients contained therein, and in particularly preferred embodiments the herein described antioxidant compound which comprises a lipophilic cationic moiety linked by a linking moiety to an antioxidant moiety, and an anionic complement (e.g., mitoQuinol $C_{10}$ mesylate), to be bioavailable upon topical administration of the composition to skin of a subject, such as a mammal, including a human, and in certain preferred embodiments a human patient having a skin condition that results from ROS production.

The topical formulations described herein deliver a therapeutically effective amount of the antioxidant compound to skin fibroblasts and keratinocytes. Preferred formulations therefore exhibit ready permeability into the skin, as can be determined according to any of a number of established methodologies known to the art for testing the skin permeability of a drug composition (see, e.g., Wagner et al., 2002 *J. Invest. Dermatol.* 118:540, and references cited therein; Bronaugh et al., 1985 *J. Pharm. Sci.* 74:64; Bosman et al., 1998 *J. Pharm. Biomed. Anal.* 17:493-499; Bosman et al., 1996 *J. Pharm Biomed Anal.* 1996 14:1015-23; Bonferoni et al., 1999 *Pharm Dev Technol.* 4:45-53; Frantz, Instrumentation and methodology for in vitro skin diffusion cells in methodology for skin absorption. In: Methods for Skin Absorption (Kemppainen & Reifenrath, Eds), CRC Press, Florida, 1990, pp. 35-59; Tojo, Design and calibration of in vitro permeation apparatus. In: Transdermal Controlled Systemic Medications (Chien Y W, Ed), Marcel Dekker, New York, 1987, 127-158; Barry, Methods for studying percutaneous absorption. In: Dermatological Formulations: Percutaneous absorption, Marcel Dekker, New York, 1983, 234-295).

Compositions that will be administered to the skin of a subject or patient may in certain embodiments take the form of one or more dosage units, where for example, a liquid-filled capsule or ampule may contain a single dosage unit, and a container of a topical formulation as described herein in aerosol form may hold a plurality of dosage units. Actual methods of preparing such dosage forms are known, or will be apparent, to those skilled in this art; for example, see *The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a skin condition that results from ROS production in skin of a subject, in accordance with the present teachings.

As noted above, the present topical formulations may take any of a wide variety of forms, and include, for example, creams, lotions, solutions, sprays, gels, ointments, pastes or the like, and/or may be prepared so as to contain liposomes, micelles, and/or microspheres. See, e.g., U.S. Pat. No. 7,205,003. For instance, creams, as is well known in the arts of pharmaceutical and cosmeceutical formulation, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions, which are preferred for delivery of cosmetic agents, are preparations to be applied to the skin surface without friction, and are typically liquid or semi-liquid preparations in which solid particles, including the active agent, are present in a water or alcohol base. Lotions are usually suspensions of solids, and preferably comprise a liquid oily emulsion of the oil-in-water type. Lotions are preferred formulations herein for treating large body areas, because of the ease of applying a more fluid composition. It is generally preferred that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like.

Solutions are homogeneous mixtures prepared by dissolving one or more chemical substances (solutes) in a liquid such that the molecules of the dissolved substance are dispersed among those of the solvent. The solution may contain other pharmaceutically acceptable and/or cosmeceutically acceptable chemicals to buffer, stabilize or preserve the solute. Common examples of solvents used in preparing solutions are ethanol, water, propylene glycol or any other pharmaceutically acceptable and/or cosmeceutically acceptable vehicles.

Gels are semisolid, suspension-type systems. Single-phase gels contain organic macromolecules distributed substantially uniformly throughout the carrier liquid, which is typically aqueous, but also, preferably, contain an alcohol, and, optionally, an oil. Preferred "organic macromolecules," i.e., gelling agents, may be chemically crosslinked polymers such as crosslinked acrylic acid polymers, for instance, the "carbomer" family of polymers, e.g., carboxypolyalkylenes, that may be obtained commercially under the Carbopol® trademark. Also preferred in certain embodiments may be hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Ointments, as also well known in the art, are semisolid preparations that are typically based on petrolatum or other petroleum derivatives. The specific ointment base to be used, as will be appreciated by those skilled in the art, is one that will provide for a number of desirable characteristics, e.g., emolliency or the like. As with other carriers or vehicles, an ointment base should be inert, stable, nonirritating, and nonsensitizing. As explained in Remington: The Science and Practice of Pharmacy, 19th Ed. (Easton, Pa.: Mack Publishing Co., 1995), at pages 1399 1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight (see, e.g., Remington, Id.).

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having one (unilamellar) or a plurality (multilamellar) of lipid walls comprising a lipid bilayer, and, in the present context, may encapsulate and/or have adsorbed to their lipid membranous surfaces one or more components of the topical formulations herein described, such as the antioxidant compounds or certain carriers or excipients. Liposomal preparations herein include cationic (positively charged), anionic (negatively charged), and neutral preparations. Cationic liposomes are readily available. For example, N[1-2,3-dioleyloxy)propyl]-N,N,N-triethylammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl-8 dodecyl ether, polyoxyl-12 dodecyl ether, nonoxynol 10, and nonoxynol 30.

Microspheres, similarly, may be incorporated into the presently described topical formulations. Like liposomes and micelles, microspheres essentially encapsulate one or more components of the present formulations. They are generally, but not necessarily, formed from lipids, preferably charged lipids such as phospholipids. Preparation of lipidic microspheres is well known in the art.

Various additives, as known to those skilled in the art, may also be included in the topical formulations. For example, solvents, including relatively small amounts of alcohol, may be used to solubilize certain formulation components. Although the mitochondrially targeted lipophilic cations of the antioxidant compounds described herein do traverse cell membranes and accumulate intracellularly within the mitochondria of skin fibroblasts and keratinocytes, it may be desirable, for certain topical formulations or in cases of particularly severe skin conditions that result from ROS, to include in the topical formulation an added skin permeation enhancer in the formulation. Examples of suitable enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer® (231, 182, 184), Tween® (20, 40, 60, 80), and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; see, e.g., U.S. Pat. No. 4,568, 343); amides and other nitrogenous compounds such as urea, dimethylacetamide (DMA), dimethylformamide (DMF), 2-pyrrolidone, 1-methyl-2-pyrrolidone, ethanolamine, diethanolamine, and triethanolamine; terpenes; alkanones; and organic acids, particularly citric acid and succinic acid. Azone® and sulfoxides such as DMSO and $C_{10}MSO$ may also be used, but are less preferred.

Most preferred skin permeation enhancers are those lipophilic co-enhancers typically referred to as "plasticizing" enhancers, i.e., enhancers that have a molecular weight in the range of about 150 to 1000 daltons, an aqueous solubility of less than about 1 wt %, preferably less than about 0.5 wt %, and most preferably less than about 0.2 wt %. The Hildebrand solubility parameter of plasticizing enhancers is in the range of about 2.5 to about 10, preferably in the range of about 5 to about 10. Preferred lipophilic enhancers are fatty esters, fatty alcohols, and fatty ethers. Examples of specific and most preferred fatty acid esters include methyl laurate, ethyl oleate, propylene glycol monolaurate, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$-$C_4$ alkane diol or triol, are substituted with one or two fatty ether substituents. Additional skin permeation enhancers will be known to those of ordinary skill in the art of topical drug delivery, and/or are described in the relevant literature. See, e.g., Percutaneous Penetration Enhancers, eds. Smith et al. (CRC Press, 1995).

Various other additives may be included in the topical formulations according to certain embodiments of the present invention, in addition to those identified above. These include, but are not limited to, additional antioxidants, astringents, perfumes, preservatives, emollients, pigments, dyes, humectants, propellants, and sunscreen agents, as well as other classes of materials whose presence may be cosmetically, medicinally or otherwise desirable. Typical examples of optional additives for inclusion in the formulations of the invention are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylauryl ether, and polysorbate 60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), α-tocopherol (Vitamin E), β-tocopherol, γ-tocopherol, δ-tocopherol, ε-tocopherol, $\zeta_1$-tocopherol, $\zeta_2$-tocopherol, η-tocopherol, and retinol (vitamin A); essential oils, ceramides, essential fatty acids, mineral oils, vegetable oils (e.g., soy bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes that may be obtained commercially under the Carbopol® trademark.

Other additives include beneficial agents such as those materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid; anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof. Other advantageously included cosmeceutically active agents may be present, for example, α-hydroxyacids, α-ketoacids, polymeric hydroxyacids, moisturizers, collagen, marine extracts, and antioxidants such as ascorbic acid (vitamin C), α-tocopherol (Vitamin E) or other tocopherols such as those described above, and retinol (vitamin A), and/or cosmetically acceptable salts, esters, amides, or other derivatives thereof. Additional cosmetic agents include those that are capable of improving oxygen supply in skin tissue, as described, for example, in WO 94/00098 and WO 94/00109. Sunscreens may also be included.

Other embodiments may include a variety of non-carcinogenic, non-irritating healing materials that facilitate treatment with the formulations of the invention. Such healing materials may include nutrients, minerals, vitamins, electrolytes, enzymes, herbs, plant extracts, glandular or animal extracts, or safe therapeutic agents that may be added to the formulation to facilitate the healing of dermal disorders. The amounts of these various additives are those conventionally used in the cosmetics field, and range, for example, from about 0.01% to about 20% of the total weight of the topical formulation.

The formulations of the invention may also include conventional additives such as opacifiers, fragrance, colorant, gelling agents, thickening agents, stabilizers, surfactants, and the like. Other agents may also be added, such as antimicrobial agents, to prevent spoilage upon storage, i.e., to inhibit growth of microbes such as yeasts and molds. Suitable antimicrobial agents are typically selected from methyl and propyl esters of p-hydroxybenzoic acid (e.g., methyl and propyl paraben), sodium benzoate, sorbic acid, imidurea, and combinations thereof. The formulations may also contain irritation-mitigating additives to minimize or eliminate the possibility of skin irritation or skin damage resulting from the chemical entity to be administered, or other components of the composition. Suitable irritation-mitigating additives include, for example: α-tocopherol; monoamine oxidase inhibitors, particularly phenyl alcohols such as 2-phenyl-1-ethanol; glycerin; salicylates; ascorbates; ionophores such as monensin; amphiphilic amines; ammonium chloride; N-acetylcysteine; capsaicin; and chloroquine. The irritation-mitigating additive, if present, may be incorporated into the topical formulation at a concentration effective to mitigate irritation or skin damage, typically representing not more than about 20 wt %, more typically not more than about 5 wt %, of the formulation.

The topical formulations may also contain, in addition to the mitochondrially targeted antioxidant compounds described herein (e.g., mitoQ-$C_{10}$ mesylate), a therapeutically effective amount of one or more additional pharmacologically active agents suitable for topical administration. Such agents may include an asymmetrical lamellar aggregate consisting of phospholipids and oxygen-loaded fluorocarbon or a fluorocarbon compound mixture, which are capable of improving oxygen supply in skin tissue, as described, for example, in International Patent Publication Nos. WO 94/00098 and WO 94/00109.

Suitable pharmacologically active agents that may be incorporated into the present topical formulations and thus topically applied, along with the mitochondrially targeted pharmaceutically and/or cosmeceutically active antioxidant compound (e.g., mitoQ-$C_{10}$ mesylate) include, but are not limited to, the following: agents that improve or eradicate pigmented or non-pigmented age spots, keratoses, and wrinkles; antimicrobial agents; antibacterial agents; antipruritic and antixerotic agents; antiinflammatory agents; local anesthetics and analgesics; corticosteroids; retinoids (e.g., retinoic acid; vitamins; hormones; and antimetabolites. Some examples of topical pharmacologically active agents include acyclovir, amphotericins, chlorhexidine, clotrimazole, ketoconazole, econazole, miconazole, metronidazole, minocycline, nystatin, neomycin, kanamycin, phenytoin, para-amino benzoic acid esters, octyl methoxycinnamate, octyl salicylate, oxybenzone, dioxybenzone, tocopherol, tocopheryl acetate, selenium sulfide, zinc pyrithione, diphenhydramine, pramoxine, lidocaine, procaine, erythromycin, tetracycline, clindamycin, crotamiton, hydroquinone and its monomethyl and benzyl ethers, naproxen, ibuprofen, cromolyn, retinoic acid, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, and 5-fluorouracil.

A pharmacological acceptable carrier may also be incorporated in the topical formulation of certain present embodiments and may be any carrier conventionally used in the art. Examples include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, and water-based mixtures and emulsion-based mixtures of such carriers.

Embodiments of the present invention may be used cosmetically, pharmaceutically, or both at the same time. Cosmetic and pharmaceutical applications may include such products as aerosols, baby products, bath oils, bubble baths, cleansers, color cosmetic products, conditioners, concealers, creams, deodorants, disinfectants, drops, eye and facial makeup, fingernail polish, foundation, gels, lip balm, lip gloss, lipstick, masks, milks, moisturizing creams, night cream, ointments, oils, perfumes, patches (including transdermal patches), powders, shampoos, shaving gels or lotions, skin benefit creams and lotions, soaps, sponges, sprays, toners, tonics, wipes, and the like. One skilled in the art will appreciate that embodiments of the present invention are not limited to the examples provided herein.

Topical formulation embodiments of the present invention may be applied regularly to whatever skin area requires treatment with the frequency and in the amount necessary to achieve the desired results. The frequency of treatment depends on the nature of the skin condition (e.g., a skin condition that results from ROS production in skin), the degree of damage or deterioration of the skin, the responsiveness of the user's skin, the strength of the active ingredients (e.g., the herein described mitochondrially targeted antioxidant compounds and optionally one or more additional pharmaceutically or cosmeceutically active ingredients) in the particular embodiment, the effectiveness of the vehicle used to deliver the active ingredients into the appropriate layer of the skin, the ease with which the formula is removed by physical contact with clothing or its removal by sweat or other intrinsic or extrinsic fluids, and the convenience to the user's lifestyle.

Typical concentrations of biochemically active substances such as the novel treatment composition described herein can range, for example, from about 0.001-30% by weight based on the total weight of the composition, to about 0.01-5.0%, and more preferably to about 0.1-2.0%. As one representative example, compositions of the present invention may be applied to the skin at a rate equal to from about 1.0 mg/cm.sup.2 of skin to about 20.0 mg/cm.sup.2 of skin. Representative examples of topical formulations include, but are not limited to, aerosols, alcohols, anhydrous bases (such as lipsticks and powders), aqeuous solutions, creams, emulsions (including either water-in-oil or oil-in-water emulsions), fats, foams, gels, hydro-alcoholic solutions, liposomes, lotions, microemulsions, ointments, oils, organic solvents, polyols, polymers, powders, salts, silicone derivatives, and waxes. Topical formulations may include, for example, chelating agents, conditioning agents, emollients, excipients, humectants, protective agents, thickening agents, or UV absorbing agents. One skilled in the art will appreciate that formulations other than those listed may be used in embodiments of the present invention.

Chelating agents may be optionally included in topical formulations, and may be selected from any agent that is suitable for use in a cosmetic composition, and may include any natural or synthetic chemical which has the ability to bind divalent cationic metals such as $Ca^{2+}$, $Mn^{2+}$, or $Mg^{2+}$. Examples of chelating agents include, but are not limited to EDTA, disodium EDTA, EGTA, citric acid, and dicarboxylic acids.

Conditioning agents may also be optionally included in topical formulations. Examples of skin conditioning agents include, but are not limited to, acetyl cysteine, N-acetyl dihydrosphingosine, acrylates/behenyl acrylate/dimethicone acrylate copolymer, adenosine, adenosine cyclic phosphate, adensosine phosphate, adenosine triphosphate, alanine, albumen, algae extract, allantoin and deriviatives, aloe barbadensis extracts, aluminum PCA, amyloglucosidase, arbutin, arginine, azulene, bromelain, buttermilk powder, butylene glycol, caffeine, calcium gluconate, capsaicin, carbocysteine, carnosine, beta-carotene, casein, catalase, cephalins, ceramides, *chamomilla recutita* (*matricaria*) flower extract, cholecalciferol, cholesteryl esters, coco-betaine, coenzyme A, corn starch modified, crystallins, cycloethoxymethicone, cysteine DNA, cytochrome C, darutoside, dextran sulfate, dimethicone copolyols, dimethylsilanol hyaluronate, DNA, elastin, elastin amino acids, epidermal growth factor, ergocalciferol, ergosterol, ethylhexyl PCA, fibronectin, folic acid, gelatin, gliadin, beta-glucan, glucose, glycine, glycogen, glycolipids, glycoproteins, glycosaminoglycans, glycosphingolipids, horseradish peroxidase, hydrogenated proteins, hydrolyzed proteins, jojoba oil, keratin, keratin amino acids, and kinetin, lactoferrin, lanosterol, lauryl PCA, lecithin, linoleic acid, linolenic acid, lipase, lysine, lysozyme, malt extract, maltodextrin, melanin, methionine, mineral salts, niacin, niacinamide, oat amino acids, oryzanol, palmitoyl hydrolyzed proteins, pancreatin, papain, PEG, pepsin, phospholipids, phytosterols, placental enzymes, placental lipids, pyridoxal 5-phosphate, quercetin, resorcinol acetate, riboflavin, RNA, *saccharomyces* lysate extract, silk amino acids, sphingolipids, stearamidopropyl betaine, stearyl palmitate, tocopherol, tocopheryl acetate, tocopheryl linoleate, ubiquinone, *vitis vinifera* (grape) seed oil, wheat amino acids, xanthan gum, and zinc gluconate. Skin conditioning agents other than those listed above may be combined with a disclosed composition or preparation provided thereby, as can be readily appreciated by one skilled in the art.

Topical formulations may also optionally include one or more emollients, examples of which include, but are not limited to, acetylated lanolin, acetylated lanolin alcohol, acrylates/C$_{10-30}$ alkyl acrylate crosspolymer, acrylates copolymer, alanine, algae extract, aloe barbadensis extract or gel, althea *officinalis* extract, aluminum starch octenylsuccinate, aluminum stearate, apricot (*prunus armeniaca*) kernel oil, arginine, arginine aspartate, *arnica montana* extract, ascorbic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (*borago officinalis*) extract, 2-bromo-2-nitropropane-1,3-diol, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, *eucalyptus globulus* oil, evening primrose (*oenothera biennis*) oil, fatty acids, fructose, gelatin, geranium *maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, macadamia *ternifolia* nut oil, magnesium stearate, magnesium sulfate, maltitol, *matricaria* (*chamomilla recutita*) oil, methyl glucose sesquistearate, methylsilanol PCA, microcrystalline wax, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12 18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, salicylic acid, sandalwood (*santalum album*) oil, serine, serum protein, sesame (*sesamum indicum*) oil, shea butter (*butyrospermum parkii*), silk powder, sodium chondroitin sulfate, sodium DNA, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

In some embodiments a topical formulation may contain a suitable excipient, which typically should have a high affinity for the skin, be well tolerated, stable, and yield a consistency that allows for easy utilization. Suitable topical excipients and vehicles can be routinely selected for a particular use by those skilled in the art, and especially with reference to one of many standard texts in the art, such as Remington's Pharmaceutical Sciences, Vol. 18, Mack Publishing Co., Easton, Pa. (1990), in particular Chapter 87 (which is herein incorporated by reference in its entirety). Optionally one or more humectants are also included in the topical formulation. Examples of humectants include, but are not limited to, amino acids, chondroitin sulfate, diglycerin, erythritol, fructose, glucose, glycerin, glycerol, glycol, 1,2,6-hexanetriol, honey, hyaluronic acid, hydrogenated honey, hydrogenated starch hydrolysate, inositol, lactitol, maltitol, maltose, mannitol, natural moisturization factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Certain embodiments contemplate topical formulations containing one or more additional skin protective agent. Examples of skin protective agents may include, but are not limited to, algae extract, allantoin, aluminum hydroxide, aluminum sulfate, betaine, *camellia sinensis* leaf extract, cerebrosides, dimethicone, glucuronolactone, glycerin, kaolin, lanolin, malt extract, mineral oil, petrolatum, potassium gluconate, and talc. One skilled in the art will readily appreciate that skin protectants other than those listed above may also be combined with a disclosed composition of the present invention or preparation provided thereby.

Surfactants may also desirably be included in certain topical formulations contemplated herein, and can be selected from any natural or synthetic surfactants suitable for use in cosmetic compositions, such as cationic, anionic, zwitterionic, or non-ionic surfactants, or mixtures thereof. (See Rosen, M., "Surfactants and Interfacial Phenomena," Second Edition, John Wiley & Sons, New York, 1988, Chapter 1, pages 4 31). Examples of cationic surfactants may include, but are not limited to, DMDAO or other amine oxides, long-chain primary amines, diamines and polyamines and their salts, quaternary ammonium salts, polyoxyethylenated long-chain amines, and quaternized polyoxyethylenated long-chain amines. Examples of anionic surfactants may include, but are not limited to, SDS; salts of carboxylic acids (e.g., soaps); salts of sulfonic acids, salts of sulfuric acid, phosphoric and polyphosphoric acid esters; alkylphosphates; monoalkyl phosphate (MAP); and salts of perfluorocarboxylic acids. Examples of zwitterionic surfactants may include, but are not limited to, cocoamidopropyl hydroxysultaine (CAPHS) and others which are pH-sensitive and require special care in designing the appropriate pH of the formula (i.e., alkylaminopropionic acids, imidazoline carboxylates, and betaines) or those which are not pH-sensitive (e.g., sulfobetaines, sultaines). Examples of non-ionic surfactants may include, but are not limited to, alkylphenol ethoxylates, alcohol ethoxylates, polyoxyethylenated polyoxypropylene glycols, polyoxyethylenated mercaptans, long-chain carboxylic acid esters, alkonolamides, tertiary acetylenic glycols, polyoxyethylenated silicones, N-alkylpyrrolidones, and alkylpolyglycosidases. Any combination of surfactants is acceptable. Certain embodiments may include at least one anionic and one cationic surfactant, or at least one cationic and one zwitterionic surfactant which are compatible, i.e., do not form complexes which precipitate appreciably when mixed.

Examples of thickening agents that may also be present in certain topical formulations include, but are not limited to, acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxytheylcellulose, hydroxypropylcellulose, hydroxpropyl starch, magnesium alginate, methylcellulose, microcrystalline cellulose, pectin, various PEG's, polyacrylic acid, polymethacrylic acid, polyvinyl alcohol, various PPG's, sodium acrylates copolymer, sodium carrageenan, xanthan gum, and yeast beta-glucan. Thickening agents other than those listed above may also be used in embodiments of this invention.

According to certain embodiments contemplated herein, a topical formulation for use in treating a skin condition that results from ROS production in the skin may comprise one or more sunscreening or UV absorbing agents. Where ultraviolet light- (UVA and UVB) absorbing properties are desired, such agents may include, for example, benzophenone, benzophenone-1, benzophenone-2, benzophenone-3, benzophenone-4, benzophenone-5, benzophenone-6, benzophenone-7, benzophenone-8, benzophenone-9, benzophenone-10, benzophenone-11, benzophenone-12, benzyl salicylate, butyl PABA, cinnamate esters, cinoxate, DEA-methoxycinnamate, diisopropyl methyl cinnamate, ethyl dihydroxypropyl PABA, ethyl diisopropylcinnamate, ethyl methoxycinnamate, ethyl PABA, ethyl urocanate, glyceryl octanoate dimethoxycinnamate, glyceryl PABA, glycol salicylate, homosalate, isoamyl p-methoxycinnamate, oxides of titanium, zinc, zirconium, silicon, manganese, and cerium, PABA, PABA esters, Parsol 1789, and isopropylbenzyl salicylate, and mixtures thereof. One skilled in the art will appreciate that sunscreening and UV absorbing or protective agents other than those listed may be used in the present invention.

Topical formulations disclosed herein are typically effective at pH values between about 2.5 and about 10.0. Preferably, the pH of the composition is at or about the following pH ranges: about pH 5.5 to about pH 8.5, about pH 5 to about pH 10, about pH 5 to about pH 9, about pH 5 to about pH 8, about pH 3 to about pH 10, about pH 3 to about pH 9, about pH 3 to about pH 8, and about pH 3 to about pH 8.5. Most preferably, the pH is about pH 7 to about pH 8. One of ordinary skill in the art may add appropriate pH adjusting ingredients to the compositions of the present invention to adjust the pH to an acceptable range.

Application

A cream, lotion, gel, ointment, paste or the like may be spread on the affected surface and gently rubbed in. A solution may be applied in the same way, but more typically will be applied with a dropper, swab, or the like, and carefully applied to the affected areas. The application regimen will depend on a number of factors that may readily be determined, such as the severity of the condition and its responsiveness to initial treatment, but will normally involve one or more applications per day on an ongoing basis. One of ordinary skill may readily determine the optimum amount of the formulation to be administered, administration methodologies and repetition rates. In general, it is contemplated that the formulations of the invention will be applied in the range of once or twice weekly up to once, twice or thrice daily.

As also discussed above, the topical formulations useful herein (e.g., pharmaceutical and/or cosmeceutical compositions) thus also contain a pharmaceutically acceptable carrier, including any suitable diluent or excipient, which includes any pharmaceutical agent that does not itself harm the subject receiving the composition, and which may be administered without undue toxicity. Pharmaceutically acceptable carriers include, but are not limited to, liquids, such as water, saline, glycerol and ethanol, and the like, and may also include viscosity enhancers (e.g., balsam fir resin) or film-formers such as colloidion or nitrocellulose solutions. A thorough discussion of pharmaceutically acceptable carriers, diluents, and other excipients is presented in REMINGTON'S PHARMACEUTICAL SCIENCES (Mack Pub. Co., N.J. current edition).

When the topical formulation is in the form of a gel- or liquid-filled capsule, for example, a gelatin capsule, it may contain, in addition to materials of the above type, a liquid carrier such as polyethylene glycol or oil. The liquid pharmaceutical and cosmeceutical compositions of the invention, whether they be solutions, suspensions or other like form, may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; additional antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

For topical administration the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical or cosmeceutical composition for topical administration. If intended for transdermal administration, the composition may include a transdermal patch or iontophoresis device. Topical formulations may contain a concentration of the compound of the invention from about 0.1 to about 10% w/v (weight per unit volume). A topical formulation may be provided in the form of a cream, lotion, solution, spray, gel, ointment, paste or the like, and/or may contain liposomes, micelles, microspheres and/or other microparticle or nanoparticle delivery elements.

The topical formulation may include an agent that binds to the antioxidant compound and thereby assists in its delivery to skin fibroblasts and keratinocytes. Suitable agents that may act in this capacity include clathrating agents such as cyclodextrins; other agents may include a protein or a liposome.

The topical formulation of the invention may also be provided in the form of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols for delivering topical formulations to the skin.

The topical formulations may be prepared by methodology well known in the pharmaceutical art. For example, a pharmaceutical composition intended to be administered to the skin as a spray, wash or rinse can be prepared by combining an antioxidant compound as described herein with sterile, distilled water so as to form a solution. A surfactant may be added to facilitate the formation of a homogeneous solution or suspension. Surfactants are compounds that non-covalently interact with the antioxidant active compound so as to facilitate dissolution or homogeneous suspension of the compound in the aqueous delivery system.

The antioxidant compounds for use in topical formulations, or their pharmaceutically acceptable salts, are administered in a therapeutically effective amount, which will vary depending upon a variety of factors including the activity of the specific antioxidant compound employed; the metabolic stability and length of action of the compound; the age, body weight, general health, sex, skin type and diet of the subject; the mode and time of administration; the rate of excretion; the drug combination; the severity of the particular skin condition that results from ROS production in skin; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

The ranges of effective doses provided herein are not intended to be limiting and represent preferred dose ranges. However, the most preferred dosage will be tailored to the individual subject, as is understood and determinable by one skilled in the relevant arts. (see, e.g., Berkow et al., eds., The Merck Manual, $16^{th}$ edition, Merck and Co., Rahway, N.J., 1992; Goodman et al., eds., Goodman and Gilman's The Pharmacological Basis of Therapeutics, $10^{th}$ edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osolci al., eds., Remington's Pharmaceutical Sciences, $18^{th}$ edition, Mack Publishing Co., Easton, Pa. (1990); Katzung, Basic and Clinical Pharmacology, Appleton and Lange, Norwalk, Conn. (1992)).

The total dose required for each treatment can be administered by multiple doses or in a single dose over the course of the day, if desired. Certain preferred embodiments contemplate a single application of the topical formulation per day. Generally, and in distinct embodiments, treatment may be initiated with smaller dosages, which are less than the optimum dose of the compound. Thereafter, the dosage is increased by small increments until the optimum effect under the circumstances is reached.

The topical formulation can be administered alone or in conjunction with other treatments and/or pharmaceuticals directed to the skin condition that results from ROS, or directed to other associated symptoms or etiologic factors. For example, and as also noted above, the topical formulation may further comprise retinoic acid. As another example, the topical formulation may comprise the mitochondrially targeted antioxidant compound described herein having a specified antioxidant moiety, or may comprise two or more such antioxidant compounds having different antioxidant moieties (e.g., a quinone or quinol such as mitoquinol, and vitamin E (tocopherol)), or may comprise one or more mitochondrially targeted antioxidant compounds as described herein in combination with other targeted or untargeted antioxidants. For instance, it is contemplated that MitoQ® (mitoquinone/mitoquinol) is capable of regenerating reduced vitamin E (tocopherol) such that inclusion in a formulation of both MitoQ and vitamin E (whether as the antioxidant moiety of a mitochondrially targeted antioxidant compound, or as an unconjugated antioxidant) may be regarded as advantageously providing a renewable source of antioxidant potential according to such an exemplary embodiment; similarly, inclusion within a topical formulation of other combinations of antioxidant moieties whereby one antioxidant may regenerate another is within related embodiments that are presently contemplated.

The recipients of the topical formulations described herein can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

For topical applications, it is preferred to administer an effective amount of a pharmaceutical or cosmeceutical composition comprising an antioxidant compound according to the invention to a target area, e.g., affected skin surfaces, at-risk areas of the skin, and the like. This amount will generally range from about 0.0001 mg to about 1 g of a compound of the invention per application, depending upon the area to be treated, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The compositions of the invention can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al, Regional Anesthesia 22 (6): 543-551 (1997), all of which are incorporated herein by reference.

The most suitable route will depend on the nature and severity of the condition being treated. Those skilled in the art are also familiar with determining topical administration methods (sprays, creams, open application, occlusive dressing, soaks, washes, etc.), dosage forms, suitable pharmaceutical excipients and other matters relevant to the delivery of the compounds to a subject in need thereof.

As noted above, according to preferred embodiments disclosed herein the above-described antioxidant compound is capable of altering (i.e., increasing or decreasing in a statistically significant manner) a detectable indicator of reactive oxygen species (ROS) in a cell or tissue of a subject, which according to highly preferred embodiments is a skin fibroblast and/or a keratinocyte in a human subject. Identification of skin fibroblasts and keratinocytes (for example, using cell type-specific histological or immunohistological markers), and detection of ROS production in such cells, for instance when present in a biological sample that is obtained from a human subject, are well known to persons having skill in the relevant arts.

An altered (i.e., increased or decreased with statistical significance) ROS level may be detectable as an indication of altered mitochondrial function. Although mitochondria are a primary source of free radicals in biological systems (see, e.g., Murphy et al., 1998 in *Mitochondria and Free Radicals in Neurodegenerative Diseases*, Beal, Howell and Bodis-Wollner, Eds., Wiley-Liss, New York, pp. 159-186 and references cited therein), the contemplated embodiments are not intended to be so limited and altered ROS production can be an indicator of a skin condition that results from ROS production in skin regardless of the particular subcellular source site. For example, numerous intracellular biochemical pathways that lead to the formation of radicals through production of metabolites such as hydrogen peroxide, nitric oxide or superoxide radical via reactions catalyzed by enzymes such as flavin-linked oxidases, superoxide dismutase or nitric oxide synthetase, are known in the art, as are methods for detecting such radicals (see, e.g., Kelver, 1993 *Crit. Rev. Toxicol.* 23:21; Halliwell B. and J. M. C. Gutteridge, *Free Radicals in Biology and Medicine,* 1989 Clarendon Press, Oxford, UK; Davies, K. J. A. and F. Ursini, *The Oxygen Paradox*, Cleup Univ. Press, Padova, IT). Altered mitochondrial function, such as failure at any step of the ETC, may also lead to the generation of highly reactive free radicals. As noted above, radicals resulting from such altered mitochondrial function or from other sources include reactive oxygen species (ROS), for example, superoxide, peroxynitrite and hydroxyl radicals, and potentially other reactive species that may be toxic to cells. Accordingly, in certain preferred embodiments a detectable level of an indicator of altered (e.g., increased or decreased in a statistically significant manner, relative to an appropriate control) ROS may be present in a biological sample that comprises a skin fibroblast and a keratinocyte from human skin of a subject that has been treated with a topical formulation containing an antioxidant compound as described herein, where the level of the indicator of altered ROS will be higher in a control sample from a subject that has not been so treated.

Methods for detecting ROS such as may be useful to confirm that an antioxidant compound is capable of altering ROS levels are known in the art and will depend on the particular ROS radical. Typically, a level of free radical production in a biological sample may be determined according to methods with which those skilled in the art will be readily familiar, including but not limited to detection and/or measurement of: glycoxidation products including pentosidine, carboxymethylysine and pyrroline; lipoxidation products including glyoxal, malondialdehyde and 4-hydroxynonenal; thiobarbituric acid reactive substances (TBARS; see, e.g., Steinbrecher et al., 1984 *Proc. Nat. Acad. Sci. USA* 81:3883; Wolff, 1993 *Br. Med. Bull.* 49:642) and/or other chemical detection means such as salicylate trapping of hydroxyl radicals (e.g., Ghiselli et al., 1998 *Meths. Mol. Biol.* 108:89; Halliwell et al., 1997 *Free Radic. Res.* 27:239) or specific adduct formation (see, e.g., Mecocci et al. 1993 *Ann. Neurol.* 34:609; Giulivi et al., 1994 *Meths. Enzymol.* 233:363) including malondialdehyde formation, protein nitrosylation, DNA oxidation including mitochondrial DNA oxidation, 8'-OH-guanosine adducts (e.g., Beckman et al., 1999 *Mutat. Res.* 424:51), protein oxidation, protein carbonyl modification (e.g., Baynes et al., 1991 *Diabetes* 40:405; Baynes et al., 1999 *Diabetes* 48:1); electron spin resonance (ESR) probes; cyclic voltametry; fluorescent and/or chemiluminescent indicators (see also e.g., Greenwald, R. A. (ed.), *Handbook of Methods for Oxygen Radical Research,* 1985 CRC Press, Boca Raton, Fla.; Acworth and Bailey, (eds.), *Handbook of Oxidative Metabolism,* 1995 ESA, Inc., Chelmsford, Mass.; Yla-Herttuala et al., 1989 *J. Clin. Invest.* 84:1086; Velazques et al., 1991 *Diabetic Medicine* 8:752; Belch et al., 1995 *Int. Angiol.* 14:385; Sato et al., 1979 *Biochem. Med.* 21:104; Traverso et al., 1998 *Diabetologia* 41:265; Haugland, 1996 *Handbook of Fluorescent Probes and Research Chemicals—Sixth Ed.*, Molecular Probes, Eugene, Oreg., pp. 483-502, and references cited therein). For example, by way of illustration and not limitation, oxidation of the fluorescent probes dichlorodihydrofluorescein diacetate and its carboxylated derivative carboxydichlorodihydrofluorescein diacetate (see, e.g., Haugland, 1996, supra) may be quantified following accumulation in cells, a process that is dependent on, and proportional to, the presence of reactive oxygen species (see also, e.g., *Molecular Probes On-line Handbook of Fluorescent Probes and Research Chemicals*, at http://www.probes.com/handbook/toc.html). Other fluorescent detectable compounds that may be used for detection of free radical (e.g., ROS) production include but are not limited to dihydrorhodamine and dihydrorosamine derivatives, cis-parinaric acid, resorufin derivatives, lucigenin and any other suitable compound that may be known to those familiar with the art.

Thus, and as also described above, free radical (e.g., ROS) mediated damage may inactivate one or more of the myriad proteins of the mitochondrial electron transport chain (ETC) and in doing so, may uncouple the mitochondrial chemiosmotic mechanism responsible for oxidative phosphorylation and ATP production. Resulting indicators of ROS may therefore comprise one or more indicators of altered mitochondrial function that are well known to the art (see, e.g., U.S. Pat. No. 6,140,067).

Additional detectable indicators of ROS may be present in a biological sample (e.g., a skin explant, biopsy, primary culture, cell line, or other clinically relevant cell- or tissue-containing specimen) that is obtained from a subject (e.g., a human having, suspected of having or being at risk for having a skin condition that results from ROS production in skin) and that comprises a skin fibroblast and/or a keratinocyte. These indicators include detection of altered (e.g., increased or decreased in a statistically significant manner) expression of one or more members of the well known matrix metalloproteinase (MMP) gene family (e.g., Heppner et al., 1996 *Am. J. Pathol.* 149:273), and detection of an altered (e.g., increased or decreased in a statistically significant manner) phosphorylation state of the well known extracellular signal-related kinase (ERK) polypeptides ERK1 or ERK2 (e.g., Seger et al., 1995 *FASEB J.* 9:726; Pages et al., 1999 *Science* 286:1374; Blume-Jensen et al., 2001 *Nature* 411:355; Boulton et al., 1990 *Science* 249:64; Boulton et al., 1991 *Cell* 65:663; Ferrell et al., 1997 *J. Biol. Chem.* 272:19008), or detection of an altered phosphorylation state of an ERK pathway molecular component (e.g., Dancey et al., 2003 *Nat. Rev. Drug. Dis.* 2:296; Grunwald et al., 2003 *J. Nat. Canc. Inst.* 95:851; Darnell, 2002 *Nat. Rev. Canc.* 2:740; Sebolt-Leopold, 2000 *Oncogene* 19:6594).

The following Examples are presented by way of illustration and not limitation.

EXAMPLES

Example 1

Topical Antioxidant Formulation

The indicated components are combined to prepare a topical antioxidant formulation cream for treating skin conditions that result from ROS production in the skin.

TABLE 1

Topical formulation: MitoQuinol-$C_{10}$-methanesulfonate (0.05% w/v) Cream

| Component | Quantity (g/mL) | Utility |
|---|---|---|
| [10-(4,5-dimethoxy-2-methyl-3,6-dioxo-1,4-cyclohexadien-1-yl)decyl] triphenylphosphonium methanesulfonate | 0.0025 | Active Antioxidant compound, mitochondrially targeted |

TABLE 1-continued

Topical formulation: MitoQuinol-$C_{10}$-methanesulfonate (0.05% w/v) Cream

| Component | Quantity (g/mL) | Utility |
|---|---|---|
| Paraffin oil light | 0.159 | Vehicle |
| Polysorbate 60 | 0.024 | Emulsifier |
| Lanolin liquid | 0.006 | Emulsifier |
| Sorbitan monostearate | 0.016 | Emulsifier |
| Cetyl alcohol 95% | 0.004 | Emulsifier |
| Stearyl alcohol | 0.03 | Thickener |
| Glycerol monostearate | 0.03 | Thickener |
| Glycerine | 0.05 | Solvent |
| Benzyl alcohol | 0.03 | Preservative |
| Water | QS to 1 mL | Solvent |

TABLE 2

Topical formulation: MitoQuinol-$C_{10}$-methanesulfonate (0.05% w/v) Cream

| Ingredient | Quantity |
|---|---|
| [10-(4,5-dimethoxy-2-methyl-3,6-dioxo-1,4-cyclohexadien-1-yl)decyl] triphenylphosphonium methanesulfonate with β-Cyclodextrin (20% w/w Mitoquinone) | 0.0025 g/ml |
| Paraffin Oil Light | 0.159 g/ml |
| Polysorbate 60 | 0.024 g/ml |
| Lanolin Liquid | 0.006 g/ml |
| Sorbitan Monostearate | 0.016 g/ml |
| Cetyl Alcohol 95% | 0.004 g/ml |
| Propyl Parahydroxybenzoate | 0.002 g/ml |
| Methyl Parahydroxybenzoate | 0.002 g/ml |
| Carbomer 974P | 0.005 g/ml |
| Glycerine | 0.050 g/ml |
| Triethanolamine | 0.005 g/ml |
| Purified Water | QS to 1 ml |

Example 2

MitoQ$_{10}$ Mesylate Suppresses ROS and Collagenase Production by Human Skin Fibroblasts in an In Vitro Skin Aging Model In photoaged human skin in vivo, skin wrinkling was accompanied by elevated collagenase levels that stimulated collagen fragmentation and ROS production. This Example describes an in vitro model of skin collagen fragmentation that was created and tested for the effects of antioxidant compounds. Materials and methods for preparing three-dimensional extracellular matrix (ECM) collagen lattices, for culturing skin fibroblasts and keratinocytes thereupon, and for treating such matrices with, and characterizing the effects on them of, matrix metalloproteinases (MMPs) have been described (see, e.g., Pilcher et al., 1997 *J. Cell Biol.* 137:1445; Notary et al., 2000 *J. Cell Biol.* 149:1309; Netzel-Arnett et al., 2002 *J. Biol. Chem.* 277:45154; Fisher et al., 2002 *Arch Dermatol.* 138:1462; Kang et al., 2003 *J. Invest. Dermatol.* 120:835; Xu et al., 2006 *Am J Pathol.* 169:823; Xu et al., 2006 *J Biol. Chem* 281:27389).

Human skin fibroblasts were cultured in three-dimensional collagen lattices, which mimicked the dermal extracellular matrix. In intact collagen lattices, dermal fibroblasts spread by attachment to the collagen, and produced relatively low levels of the collagenase known as matrix metalloproteinase-1 (MMP1). Fragmentation of the collagen lattices by exogenously introduced collagenase (MMP1) caused the fibroblasts to collapse (i.e., lose mechanical tension) and also caused the fibroblasts to produce elevated levels of matrix metalloproteinase-1. In addition, collagenase-induced collagen fragmentation caused fibroblasts to generate relatively high levels of ROS, similar to that observed in aged human skin in vivo (FIG. 1).

Figure 2:
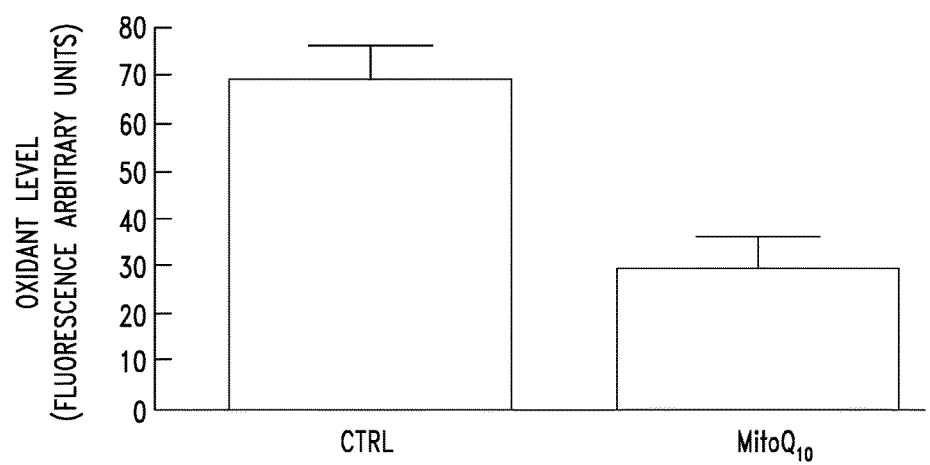
FIG. 2 shows effects of MitoQ$_{10}$ mesylate on ROS production in human skin fibroblasts cultured in three-dimensional collagen lattices, following treatment with collagenase (MMP1).
Figure 3:
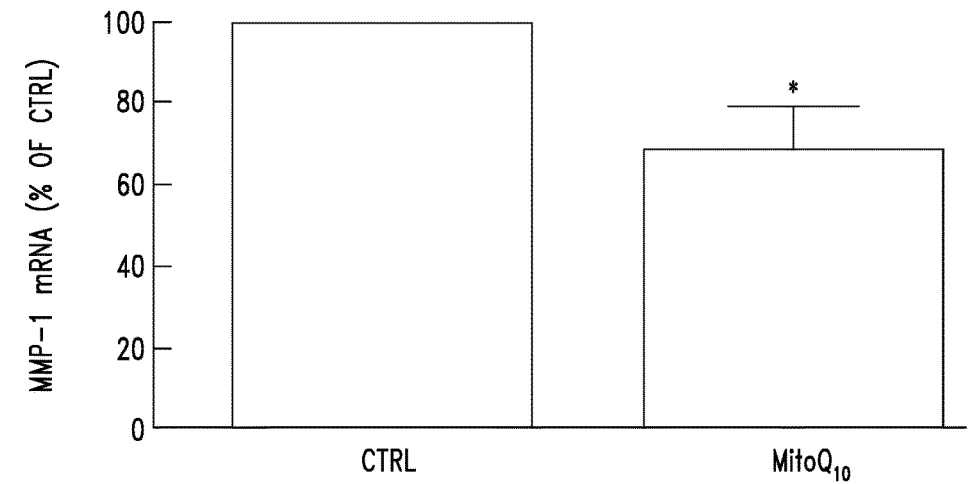
FIG. 3 shows effects of MitoQ$_{10}$ mesylate on MMP1 expression in human skin fibroblasts cultured in three-dimensional collagen lattices, following treatment with collagenase (MMP1).
Figure 3:
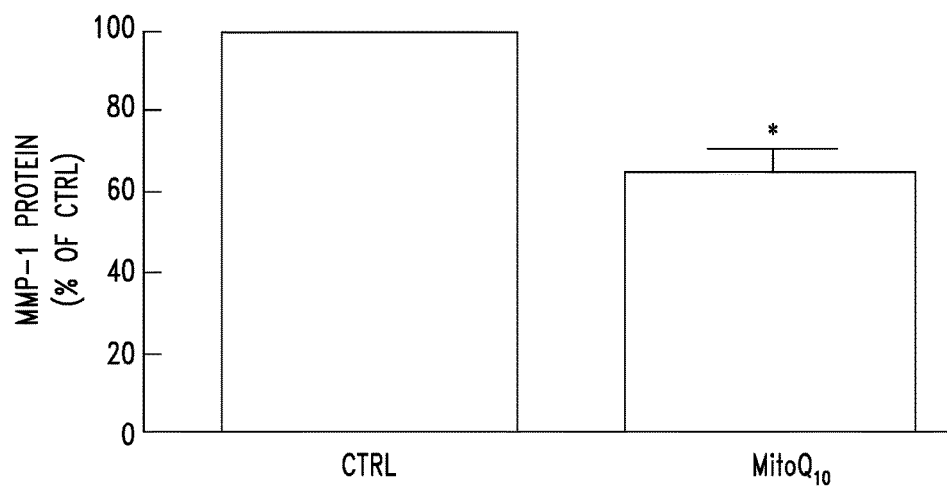

When human skin fibroblasts were cultured in collagenase-fragmented three-dimensional collagen lattices in the absence or presence of 1 nM MitoQ$_{10}$ mesylate ("MitoQ$_{10}$", [10-(4,5-dimethoxy-2-methyl-3,6-dioxo-1,4-cyclohexadien-1-yl)decyl] triphenylphosphonium methanesulfonate), oxidant (ROS) levels were significantly reduced when MitoQ$_{10}$ was present (FIG. 2) relative to controls, as were levels of matrix metalloproteinase-1 expression assessed by quantifying MMP1 mRNA and by quantifying MMP1 protein (FIG. 3). These data were consistent with a reduction in oxidative stress in skin fibroblasts when MitoQ10 was present, thereby decreasing MMP expression and hence MMP-catalyzed collagen fragmentation.

Example 3

MitoQ$_{10}$ Mesylate Suppresses UV Irradiation-Induced Activation of ERK in Human Keratinocytes Ultraviolet (UV) irradiation causes skin photoaging and has been reported to activate mitogen-activated protein (MAP) kinase signal transduction pathways. (Fisher et al., 1998 *J. Clin. Invest.* 101:1432; Kang et al., 2003 *J. Invest. Dermatol.* 120:835). The mechanism of UV activation of the epidermal growth factor receptor (EGFR) in such pathways remains unknown, although a role for ROS has been implicated (Xu et al., 2006 *Am. J. Pathol.* 169:823; Xu et al., 2006 *J. Biol. Chem.* 281:27389). This Example describes an in vitro model of UV-induced signal transduction in human keratinocytes. Publications describing exemplary materials and methods that were adapted to perform these experiments include e.g., Pilcher et al., 1997 *J. Cell Biol.* 137:1445; Notary et al., 2000 *J. Cell Biol.* 149:1309; Netzel-Arnett et al., 2002 *J. Biol. Chem.* 277:45154; Fisher et al., 2002 *Arch Dermatol.* 138:1462; Kang et al., 2003 *J. Invest. Dermatol.* 120:835; Xu et al., 2006 *Am J Pathol.* 169:823; Xu et al., 2006 *J Biol. Chem* 281:27389.

Exposure of cultured human keratinocytes to UV irradiation activated ERK MAP kinase, as evidenced by elevated levels of phosphorylated ERK polypeptide in immunoprecipitates from UV-irradiated keratinocytes relative to untreated control keratinocytes. (FIG. 4)

Figure 4:
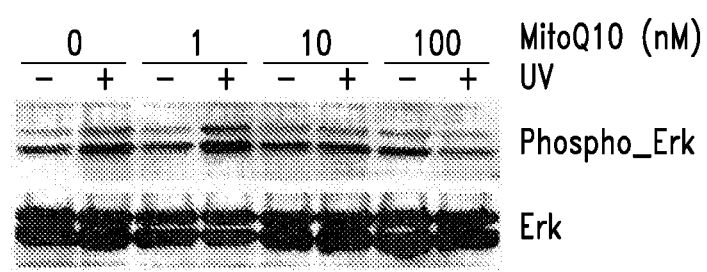
FIG. 4 shows effects of MitoQ$_{10}$ mesylate on ERK phosphorylation in cultured human keratinocytes.

As also shown in FIG. 4, pretreatment of the keratinocytes with the indicated concentrations of MitoQ$_{10}$ mesylate substantially inhibited the activation of ERK MAP kinase by subsequent UV irradiation. FIG. 4 (upper panel, first and second lanes from left) shows that UV irradiation increased phosphorylation of ERK1 (upper band in upper panel) and ERK2 (lower band in upper panel). Incubation of keratinocytes with the indicated concentrations of MitoQ$_{10}$, prior to UV irradiation, significantly reduced ERK1 and ERK2 phosphoyrlation. The lower panel indicates that the amounts of Erk1 and Erk2 in the keratinocytes were not altered by exposure to UV irradiation, nor by exposure to MitoQ$_{10}$. These data were consistent with a reduction in UV-induced oxidative stress in human keratinocytes when MitoQ$_{10}$ was present during UV irradiation.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating a skin condition that results from reactive oxygen species production in skin of a subject having the skin condition that results from reactive oxygen species production in skin, the method comprising:
   applying to stratum corneum of the skin of the subject a topical formulation that comprises
      (a) about 0.01% to about 5.0% by weight of an antioxidant compound which comprises a lipophilic cationic moiety linked by a linking moiety to a quinone antioxidant moiety, and an anionic complement for said cationic moiety, the antioxidant compound being a compound of formula II:

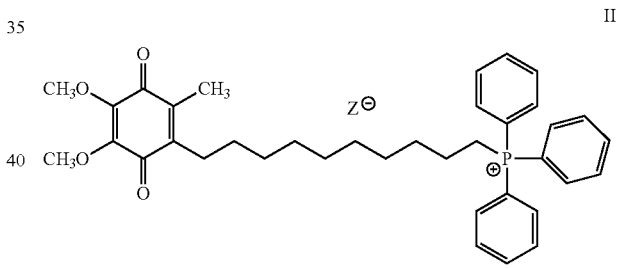

II or its quinol form, wherein Z is the anionic complement and is selected from the group consisting of methanesulfonate, p-toluenesulfonate, ethanesulfonate, benzenesulfonate and 2-naphthalenesulfonate,
   and
      (b) a pharmaceutical excipient or carrier for topical use,
   wherein the formulation delivers a therapeutically effective amount of the antioxidant compound to skin dermal fibroblasts and epidermal keratinocytes in the skin of the subject and the lipophilic cationic moiety is capable of mitochondrially targeting the antioxidant moiety,
   wherein the antioxidant compound is capable of altering (i) a detectable indicator of reactive oxygen species in a human skin fibroblast, and (ii) a detectable indicator of reactive oxygen species in a human skin keratinocyte, and
   wherein the skin condition that results from reactive oxygen species production is characterized by alteration of at least one of (i) a detectable indicator of reactive oxygen species in a human skin fibroblast, and (ii) a detectable indicator of reactive oxygen species in a human skin keratinocyte, and thereby treating the skin condition that results from reactive oxygen species production in skin.

2. The method of claim 1 wherein the topical formulation further comprises retinoic acid.

3. The method of claim 1 wherein the pharmaceutically acceptable anion is methanesulfonate.

4. The method of claim 1 wherein the antioxidant compound has the formula:

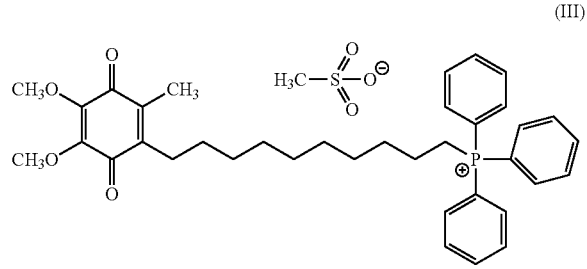

(III)

or its quinol form.

5. The method of claim 1 wherein the pharmaceutical excipient or carrier comprises cyclodextrin.

6. The method of claim 5 wherein the antioxidant compound and cyclodextrin are present at a compound-to-cyclodextrin molar ratio that is selected from (i) about 10:1 to about 1:10, (ii) from about 5:1 to about 1:5, (iii) from about 4:1 to about 1:4, (iv) from about 2:1 to about 1:2, (v) about 1:1 and (vi) about 1:2.

7. The method of claim 6 wherein the cyclodextrin is β-cyclodextrin.

8. The method of claim 7 wherein the antioxidant compound and cyclodextrin are present at a compound-to-cyclodextrin molar ratio that is about 1:2.

9. The method of claim 1 wherein the skin condition that results from reactive oxygen species production is age-related skin damage.

10. The method of claim 9 wherein the age-related skin damage comprises skin photoaging.

11. The method of claim 10 wherein skin photoaging comprises one or more of wrinkling, scar tissue deposition, altered skin elasticity, altered skin color, altered skin texture, altered skin thickness, angioma, telangiectasia, sunburn, dryness, itchiness, neoplasia and precancerous growth.

12. The method of claim 1 wherein the skin condition that results from reactive oxygen species production comprises a skin infection.

13. The method of claim 12 wherein the skin infection comprises at least one of a bacterial infection, a viral infection, a parasitic infection and a fungal infection.

14. The method of claim 1 wherein the skin condition that results from reactive oxygen species production comprises one or more of acne, amyloidosis, a benign skin tumor, a blister or ulcer, bullous disease, skin cancer, dermatitis, eczema, inflammation, ichthyosis, an insect bite or insect sting, keratosis pilaris, pruritis, psoriasis, a scaling disease, a rash, vitiligo and a sweat gland disorder.

15. The method of claim 1 wherein the antioxidant compound is capable of altering (i) at least one detectable indicator of reactive oxygen species in a human skin fibroblast that is selected from the group consisting of reactive oxygen species generation, matrix metalloproteinase expression and an extracellular signal-related kinase (ERK) phosphorylation state, and (ii) at least one detectable indicator of reactive oxygen species in a human skin keratinocyte that is selected from the group consisting of reactive oxygen species generation, matrix metalloproteinase expression and an extracellular signal-related kinase (ERK) phosphorylation state.

16. The method of claim 1 wherein the skin condition that results from reactive oxygen species production comprises one or more condition selected from the group consisting of erythema, skin redness and inflammation caused by laser surgery, radiation therapy, sun burn, rosaceae, a burn or sepsis.

17. A method of promoting topical wound healing in skin of a subject in need thereof, the method comprising:
applying to stratum corneum of the skin of the subject a topical formulation that comprises
(a) about 0.01% to about 5.0% by weight of an antioxidant compound which comprises a lipophilic cationic moiety linked by a linking moiety to a quinone antioxidant moiety, and an anionic complement for said cationic moiety, the antioxidant compound being a compound of formula II:

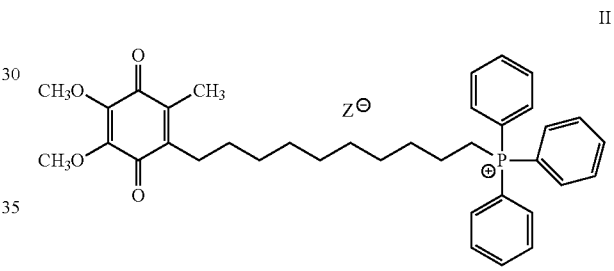

II or its quinol form, wherein Z is the anionic complement and is selected from the group consisting of methanesulfonate, p-toluenesulfonate, ethanesulfonate, benzenesulfonate and 2-naphthalellesulfonate,
and
(b) a pharmaceutical excipient or carrier for topical use,
wherein the formulation delivers a therapeutically effective amount of the antioxidant compound to skin dermal fibroblasts and epidermal keratinocytes in the skin of the subject and the lipophilic cationic moiety is capable of mitochondrially targeting the antioxidant moiety, and
wherein the antioxidant compound is capable of altering (i) a detectable indicator of reactive oxygen species in a human skin fibroblast, and (ii) a detectable indicator of reactive oxygen species in a human skin keratinocyte,
and thereby promoting topical wound healing in the skin of the subject.

18. The method of claim 17 wherein the topical formulation further comprises retinoic acid.

19. The method of claim 17 wherein the pharmaceutically acceptable anion is methanesulfonate.

* * * * *

UNITED STATES PATENT AND TRADEMARK OFFICE
CERTIFICATE OF CORRECTION

PATENT NO. : 10,085,966 B2
APPLICATION NO. : 15/400510
DATED : October 2, 2018
INVENTOR(S) : Michael Patrick Murphy et al.

It is certified that error appears in the above-identified patent and that said Letters Patent is hereby corrected as shown below:

In the Claims

Column 36, Claim 17, Line 42:
"2-naphthalellesulfonate," should read --2-naphthalenesulfonate,--.

Signed and Sealed this
Third Day of September, 2019

Andrei Iancu
*Director of the United States Patent and Trademark Office*